US007029878B2

(12) United States Patent
Marsh

(10) Patent No.: US 7,029,878 B2
(45) Date of Patent: Apr. 18, 2006

(54) MELANIN CONCENTRATING HORMONE RECEPTOR CHIMERIC AND FUSION PROTEINS

(75) Inventor: Donald J. Marsh, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 457 days.

(21) Appl. No.: 10/221,461

(22) PCT Filed: Mar. 14, 2001

(86) PCT No.: PCT/US01/08071

§ 371 (c)(1),
(2), (4) Date: Sep. 12, 2002

(87) PCT Pub. No.: WO01/68706

PCT Pub. Date: Sep. 20, 2001

(65) Prior Publication Data

US 2003/0092902 A1 May 15, 2003

Related U.S. Application Data

(60) Provisional application No. 60/189,698, filed on Mar. 15, 2000.

(51) Int. Cl.
  *C07K 14/705* (2006.01)
  *C07K 19/00* (2006.01)
  *C12N 15/62* (2006.01)
  *G01N 33/567* (2006.01)
(52) U.S. Cl. .................. 435/69.7; 435/7.21; 530/350; 536/23.4
(58) Field of Classification Search ............. 435/7.21, 435/69.7; 530/350; 536/23.4
See application file for complete search history.

(56) References Cited

U.S. PATENT DOCUMENTS

| 5,625,048 A | 4/1997 | Tsien et al. |
| 5,777,079 A | 7/1998 | Tsien et al. |
| 5,804,387 A | 9/1998 | Cormack et al. |

OTHER PUBLICATIONS

Buggy et al. "Glucagon-Glucagon-like Peptide I Receptor Chimeras Reveal Domains That Determine Specificity of Glucagon Binding", Mar. 31, 1995, J. Biol. Chem. 270(13): 7474-7478.*
Holtmann et al. "Critical Contributions of Amino-terminal Extracellular Domains in Agonist Binding and Activation of Secretin an Vasoactive Intestinal Polypeptide Receptors", Jun. 16, 1995, J. Biol. Chem. 270(24):14394-14398.*
Kim et al. "Random Chimeragenesis of G protein-coupled Receptors", Nov. 18, 1994, J. Biol. Chem. 269(46):28724-28731.*
Meng et al. "Mapping the Receptor Domains Critical for the Binding Selectivity of delta-opioid Receptor Ligands", 1996, Euro. J Pharmacol. 311:285-292.*
Schioth et al., "Chimeric Melatonin MC1 and MC3 Receptors: Identification of domains Participating in Binding of Melanocyte-Stimulating Hormone Peptides", 1998, Mol. Pharmacol. 54:154-161.*
Takagi et al. "Structural Basis of G Protein Specificity of Human Endothelial Receptors", Aug. 28, 1995, J. Biol. Chem. 270(17):10072-10078.*
Gether et al. "Chimeric NK1 (Substance P)/NK3 (Neuromedin B) Receptors", Apr. 15, 1993, J. Biol. Chem. 268(11):7893-7898.*
Wu et al. "First Intracellular Loop of the Human Cholecystokinin-A Receptor Is Essential for Cyclic AMP Signalling in Transfected HEK-293 Cells", Apr. 4, 1997, J. Biol. Chem. 272(14):9037-9042.*
Awaji, T. et al. "Real-Time Optical Monitoring of Lingand-Mediated Internalization of α1b-Adrenoceptor with Green Fluorescent Protein", Molecular Endocrinology, 1998, vol. 12, pp. 1099-1111.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Barak, L. et al. "Internal Trafficking and Surface Mobility of a Functionally Intact b2-Adrenergic Receptor-Green Fluorescent Protein Conjugate", Molecular Pharmacology, 1997, vol. 51, pp. 177-184.
Breton, C. et al. "Isolation and characterization of the human melanin-concentrating hormone gene and a variant gene", Molecular Brain Research, 1993, vol. 18, pp. 297-310.
Brock, R. et al. "Rapid characterization of green fluorescent protein fusion proteins on the molecular and cellular level by fluorescence correlation microscopy", Proc. Natl. Acad. Sci. USA, 1999, vol. 96, pp. 10123-10128.
Button, D. et al. "Aequorin-expressing mammalian cell lines used to report Ca2+ mobilization", Cell Calcium, 1993, vol. 14, pp. 663-671.

(Continued)

*Primary Examiner*—John Ulm
(74) *Attorney, Agent, or Firm*—Sheldon O. Heber; Jack L. Tribble

(57) ABSTRACT

The present invention features melanin concentrating hormone receptor (MCH-R) chimeric and fusion proteins. MCH-R chimeric proteins comprise an MCH-R polypeptide region made up of at least two or more polypeptide regions characteristic of MCH-R found in different species. MCH-R fusion proteins comprise an MCH-R polypeptide region and a fluorescent protein region.

19 Claims, 3 Drawing Sheets

OTHER PUBLICATIONS

Chambers, J. et al. "Melanin-concentrating hormone is the cognate ligand for the orphan G-protein-coupled receptor SLC-1", Nature, 1999, vol. 400, pp. 261-265.

Clontech Laboratories, Inc., Living Colors Fluorescent Proteins, 1998.

Clontech Laboratories, Inc., Products: Living Colors Fluorescent Protein Vectors, Feb. 2, 2000.

Clontech Laboratories, Inc., Technical Info.: pEGFP-F Vector, Feb. 29, 2000.

Clontech Laboratories, Inc., Technical Info.: pEGFP-N3 Vector, Feb. 29, 2000.

Cormack, B. et al. "FACS-optimized mutants of the green fluorescent protein (GFP)", Gene, 1996, vol. 173, pp. 33-38.

Cornea, A. et al. "Simultaneous and Independent Visualization of the Gonadotropin-Releasing Hormone Receptor and Its Ligand: Evidence for Independent Processing and Recycling in Living Cells", Endocrinology, 1999, vol. 140, pp. 4272-4280.

Doherty, A. et al. "Rapid internalization and surface expression of a functional, fluorescently tagged G-protein-coupled glutamate receptor", Biochem J., 1999, vol. 341, pp. 415-422.

Feighner, S. et al. "Receptor for Motilin Identified in the Human Gastrointestinal System", Science, 1999, vol. 284, pp. 2184-2188.

Groarke, D. et al. "Visualization of Agonist-induced Association and Trafficking of Green Fluorescent Protein-tagged Forms of Both b-Arrestin-1 and the Thyrotropin-releasing Hormone Receptor-1", The Journal of Biological Chemistry, 1999, vol. 274, pp. 23263-23269.

Kallal, L. et al. "Visualization of Agonist-induced Sequestration and Down-regulation of a Green Fluorescent Protein-tagged b2-Adrenergic Receptor", The Journal of Biological Chemistry, 1998, vol. 273, pp. 322-328.

Knigge, K. et al. "Melanotropic Peptides in the Mammalian Brain: The Melanin-Concentrating Hormone", Peptides, 1996, vol. 17, pp. 1063-1073.

Kobilka, B. et al. "Chimeric α2-β2-Adrenergic Receptors: Delineation of Domains Involved in Effector Coupling and Ligand Binding Specificity", Science, 1988, vol. 240, pp. 1310-1316.

Lembo, P. et al. "The receptor for the orexigenic peptide melanin-concentrating hormone is a G-protein-coupled receptor", Nature Cell Biology, 1999, vol. 1, p. 267-271.

Lin, X, et al. "Visualization of unoccupied and occupied gonadotropin-releasing hormone receptors in living cells", Molecular and Cellular Endocrinology, 1998, vol. 146, pp. 27-37.

Mombaerts, P. et al. "Visualizing an Olfactory Sensory Map", Cell, 1996, vol. 87, pp. 675-686.

Nahon, J. "The Melanin-Concentrating Hormone: From the Peptide to the Gene", Critical Reviews in Neurobiology, 1994, vol. 8, pp. 221-262.

Nelson, S. et al. "Characterization of an Instrinsically Fluorescent Gonadotropin-Releasing Hormone Receptor and Effects of Ligand Binding on Receptor Lateral Diffusion", Endocrinology, 1999, vol. 140, pp. 950-957.

Presse, F. et al. "Structure of the Human Melanin Concentrating Hormone mRNA", Molecular Endocrinology, 1990, vol. 4, pp. 632-637.

Qu, D. et al., "A role for melanin-concentrating hormone in the central regulation of feeding behaviour", Nature, 996, vol. 380, pp. 243-247.

Rodriguez, I. et al. "Variable Patterns of Axonal Projections of Senosory Neurons in the Mouse Vomeronasal System", Cell, 1999, vol. 97, pp. 199-208.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Spergel, D. et al. "GABA- and Glutamate-Activated Channels in Green Fluorescent Protein Tagged Gonadotropin-Releasing Hormone Neurons in Transgenic Mice", The Journal of Neuroscience, 1999, vol. 19, pp. 2037-2050.

Tarasova, N. et al. "Visualization of G Protein-coupled Receptor Trafficking with the Aid of the Green Fluorescent Protein", The Journal of Biochemical Chemistry, 1997, vol. 272, pp. 14817-14824.

Tarasova, N. et al. "Spontaneous and Ligand-induced Trafficking of CXC-Chemokine Receptor 4", The Journal of Biological Chemistry, 1998, vol. 273, pp. 15883-15886.

Yang, T. et al. "Optimized codon usage and chromophore mutations provide enhanced sensitivity with the green fluorescent protein", Nucleic Acids Research, 1996, vol. 24, pp. 4592-4593.

Zuo, J. et al. "Visualization of a9 acetylcholine receptor expression in hair cells of transgenic mice containing a modified bacterial artificial chromosome", Proc. Natl. Acad. Sci. USA, 1999, vol. 96, pp. 14100-14105.

* cited by examiner

SEQUENCE LISTING

```
<160> NUMBER OF SEQ ID NOS: 37
<210> SEQ ID NO 1
<211> LENGTH: 422
<212> TYPE: PRT
<213> ORGANISM: Human

<400> SEQUENCE: 1

Met Ser Val Gly Ala Met Lys Lys Gly Val Gly Arg Ala Val Gly Leu
 1               5                  10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
        50                  55                  60

Thr Gly Thr Gly Trp Met Asp Leu Glu Ala Ser Leu Leu Pro Thr Gly
 65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile Met
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285

Pro Phe Val Val Ile Thr Ala Ala Tyr Val Arg Ile Leu Gln Arg Met
    290                 295                 300

Thr Ser Ser Val Ala Pro Ala Ser Gln Arg Ser Ile Arg Leu Arg Thr
```

```
            305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
                355                 360                 365

Gly Tyr Ala Asn Ser Cys Leu Asn Pro Phe Val Tyr Ile Val Leu Cys
            370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
                420

<210> SEQ ID NO 2
<211> LENGTH: 353
<212> TYPE: PRT
<213> ORGANISM: Human

<400> SEQUENCE: 2

Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
                20                  25                  30

Thr Gly Ser Ile Ser Tyr Ile Asn Ile Ile Met Pro Ser Val Phe Gly
            35                  40                  45

Thr Ile Cys Leu Leu Gly Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255
```

```
Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
                340                 345                 350

Thr

<210> SEQ ID NO 3
<211> LENGTH: 353
<212> TYPE: PRT
<213> ORGANISM: Mouse

<400> SEQUENCE: 3

Met Asp Leu Gln Ala Ser Leu Leu Ser Thr Gly Pro Asn Ala Ser Asn
  1               5                  10                  15

Ile Ser Asp Gly Gln Asp Asn Phe Thr Leu Ala Gly Pro Pro Pro Arg
            20                  25                  30

Thr Arg Ser Val Ser Tyr Ile Asn Ile Ile Met Pro Ser Val Phe Gly
            35                  40                  45

Thr Ile Cys Leu Leu Gly Ile Val Gly Asn Ser Thr Val Ile Phe Ala
            50                  55                  60

Val Val Lys Lys Ser Lys Leu His Trp Cys Ser Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
            130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
            210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270
```

```
Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr

<210> SEQ ID NO 4
<211> LENGTH: 353
<212> TYPE: PRT
<213> ORGANISM: Artificial Sequence
<220> FEATURE:
<223> OTHER INFORMATION: Human short form/mouse species chimeric MCH1R

<400> SEQUENCE: 4

Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
                20                  25                  30

Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
```

```
                275                 280                 285
Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
                340                 345                 350

Thr

<210> SEQ ID NO 5
<211> LENGTH: 422
<212> TYPE: PRT
<213> ORGANISM: Artificial Sequence
<220> FEATURE:
<223> OTHER INFORMATION: Human long form/mouse species chimeric MCH1R

<400> SEQUENCE: 5

Met Ser Val Gly Ala Met Lys Lys Gly Val Gly Arg Ala Val Gly Leu
1               5                   10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
        50                  55                  60

Thr Gly Thr Gly Trp Met Asp Leu Glu Ala Ser Leu Leu Pro Thr Gly
65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile Met
                100                 105                 110

Pro Ser Val Phe Gly Thr Ile Cys Leu Leu Gly Ile Ile Gly Asn Ser
            115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
        195                 200                 205

Asp Arg Tyr Leu Ala Thr Val His Pro Ile Ser Ser Thr Lys Phe Arg
    210                 215                 220

Lys Pro Ser Met Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285
```

```
Pro Phe Val Val Ile Thr Ala Ala Tyr Val Lys Ile Leu Gln Arg Met
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
                340                 345                 350

Arg Pro Thr Leu Thr Phe Val Tyr Leu Tyr Asn Ala Ala Ile Ser Leu
                355                 360                 365

Gly Tyr Ala Asn Ser Cys Leu Asn Pro Phe Val Tyr Ile Val Leu Cys
                370                 375                 380

Glu Thr Phe Arg Lys Arg Leu Val Leu Ser Val Lys Pro Ala Ala Gln
385                 390                 395                 400

Gly Gln Leu Arg Thr Val Ser Asn Ala Gln Thr Ala Asp Glu Glu Arg
                405                 410                 415

Thr Glu Ser Lys Gly Thr
                420

<210> SEQ ID NO 6
<211> LENGTH: 238
<212> TYPE: PRT
<213> ORGANISM: Aequorea Victoria

<400> SEQUENCE: 6

Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
                 20                  25                  30

Gly Glu Gly Asp Ala Thr Tyr Gly Lys Leu Thr Leu Lys Phe Ile Cys
             35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
```

```
                225                 230                 235
```

<210> SEQ ID NO 7
<211> LENGTH: 239
<212> TYPE: PRT
<213> ORGANISM: Artificial Sequence
<220> FEATURE:
<223> OTHER INFORMATION: GFP derivative

<400> SEQUENCE: 7

```
Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 8
<211> LENGTH: 239
<212> TYPE: PRT
<213> ORGANISM: Artificial Sequence
<220> FEATURE:
<223> OTHER INFORMATION: GFP derivative

<400> SEQUENCE: 8

```
Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Lys Val Tyr Ile Thr Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 239
<212> TYPE: PRT
<213> ORGANISM: Artificial Sequence
<220> FEATURE:
<223> OTHER INFORMATION: GFP derivative

<400> SEQUENCE: 9

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Phe Gly Tyr Gly Val Gln Cys Phe Ala Arg Tyr Pro Asp His Met Arg
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 10
<211> LENGTH: 239
<212> TYPE: PRT
<213> ORGANISM: Artificial Sequence
<220> FEATURE:
<223> OTHER INFORMATION: GFP derivative

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 11
<211> LENGTH: 604
<212> TYPE: PRT
<213> ORGANISM: Artificial Sequence
<220> FEATURE:
<223> OTHER INFORMATION: Mouse MCH1R-linker-EGFP

<400> SEQUENCE: 11

Met Asp Leu Gln Ala Ser Leu Leu Ser Thr Gly Pro Asn Ala Ser Asn
1               5                   10                  15

Ile Ser Asp Gly Gln Asp Asn Phe Thr Leu Ala Gly Pro Pro Pro Arg
            20                  25                  30
```

```
Thr Arg Ser Val Ser Tyr Ile Asn Ile Ile Met Pro Ser Val Phe Gly
         35                  40                  45
Thr Ile Cys Leu Leu Gly Ile Val Gly Asn Ser Thr Val Ile Phe Ala
     50                  55                  60
Val Val Lys Lys Ser Lys Leu His Trp Cys Ser Asn Val Pro Asp Ile
 65                  70                  75                  80
Phe Ile Ile Asn Leu Ser Val Val Asp Leu Leu Phe Leu Leu Gly Met
                 85                  90                  95
Pro Phe Met Ile His Gln Leu Met Gly Asn Gly Val Trp His Phe Gly
            100                 105                 110
Glu Thr Met Cys Thr Leu Ile Thr Ala Met Asp Ala Asn Ser Gln Phe
        115                 120                 125
Thr Ser Thr Tyr Ile Leu Thr Ala Met Ala Ile Asp Arg Tyr Leu Ala
    130                 135                 140
Thr Val His Pro Ile Ser Ser Thr Lys Phe Arg Lys Pro Ser Met Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Lys Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
    275                 280                 285
Phe Val Tyr Leu Tyr Asn Ala Ala Ile Ser Leu Gly Tyr Ala Asn Ser
    290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Thr
                325                 330                 335
Val Ser Asn Ala Gln Thr Ala Asp Glu Glu Arg Thr Glu Ser Lys Gly
            340                 345                 350
Thr Val Asp Gly Thr Ala Gly Pro Gly Ser Ile Ala Thr Met Val Ser
        355                 360                 365
Lys Gly Glu Glu Leu Phe Thr Gly Val Val Pro Ile Leu Val Glu Leu
    370                 375                 380
Asp Gly Asp Val Asn Gly His Lys Phe Ser Val Ser Gly Glu Gly Glu
385                 390                 395                 400
Gly Asp Ala Thr Tyr Gly Lys Leu Thr Leu Lys Phe Ile Cys Thr Thr
                405                 410                 415
Gly Lys Leu Pro Val Pro Trp Pro Thr Leu Val Thr Thr Leu Thr Tyr
            420                 425                 430
Gly Val Gln Cys Phe Ser Arg Tyr Pro Asp His Met Lys Gln His Asp
        435                 440                 445
```

```
Phe Phe Lys Ser Ala Met Pro Glu Gly Tyr Val Gln Glu Arg Thr Ile
    450                 455                 460
Phe Phe Lys Asp Asp Gly Asn Tyr Lys Thr Arg Ala Glu Val Lys Phe
465                 470                 475                 480
Glu Gly Asp Thr Leu Val Asn Arg Ile Glu Leu Lys Gly Ile Asp Phe
                485                 490                 495
Lys Glu Asp Gly Asn Ile Leu Gly His Lys Leu Glu Tyr Asn Tyr Asn
            500                 505                 510
Ser His Asn Val Tyr Ile Met Ala Asp Lys Gln Lys Asn Gly Ile Lys
        515                 520                 525
Val Asn Phe Lys Ile Arg His Asn Ile Glu Asp Gly Ser Val Gln Leu
    530                 535                 540
Ala Asp His Tyr Gln Gln Asn Thr Pro Ile Gly Asp Gly Pro Val Leu
545                 550                 555                 560
Leu Pro Asp Asn His Tyr Leu Ser Thr Gln Ser Ala Leu Ser Lys Asp
                565                 570                 575
Pro Asn Glu Lys Arg Asp His Met Val Leu Leu Glu Phe Val Thr Ala
            580                 585                 590
Ala Gly Ile Thr Leu Gly Met Asp Glu Leu Tyr Lys
        595                 600
```

<210> SEQ ID NO 12
<211> LENGTH: 592
<212> TYPE: PRT
<213> ORGANISM: Artificial Sequence
<220> FEATURE:
<223> OTHER INFORMATION: Mouse MCH1R/EGFP

<400> SEQUENCE: 12

```
Met Asp Leu Gln Ala Ser Leu Leu Ser Thr Gly Pro Asn Ala Ser Asn
1               5                   10                  15
Ile Ser Asp Gly Gln Asp Asn Phe Thr Leu Ala Gly Pro Pro Pro Arg
            20                  25                  30
Thr Arg Ser Val Ser Tyr Ile Asn Ile Ile Met Pro Ser Val Phe Gly
        35                  40                  45
Thr Ile Cys Leu Leu Gly Ile Val Gly Asn Ser Thr Val Ile Phe Ala
    50                  55                  60
Val Val Lys Lys Ser Lys Leu His Trp Cys Ser Asn Val Pro Asp Ile
65                  70                  75                  80
Phe Ile Ile Asn Leu Ser Val Val Asp Leu Leu Phe Leu Leu Gly Met
                85                  90                  95
Pro Phe Met Ile His Gln Leu Met Gly Asn Gly Val Trp His Phe Gly
            100                 105                 110
Glu Thr Met Cys Thr Leu Ile Thr Ala Met Asp Ala Asn Ser Gln Phe
        115                 120                 125
Thr Ser Thr Tyr Ile Leu Thr Ala Met Ala Ile Asp Arg Tyr Leu Ala
    130                 135                 140
Thr Val His Pro Ile Ser Ser Thr Lys Phe Arg Lys Pro Ser Met Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
```

```
Thr Leu Tyr Gln Phe Phe Leu Ala Phe Ala Leu Pro Phe Val Ile
    210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr Met Val Ser Lys Gly Glu Glu Leu Phe Thr Gly Val Val Pro Ile
        355                 360                 365

Leu Val Glu Leu Asp Gly Asp Val Asn Gly His Lys Phe Ser Val Ser
    370                 375                 380

Gly Glu Gly Glu Gly Asp Ala Thr Tyr Gly Lys Leu Thr Leu Lys Phe
385                 390                 395                 400

Ile Cys Thr Thr Gly Lys Leu Pro Val Pro Trp Pro Thr Leu Val Thr
                405                 410                 415

Thr Leu Thr Tyr Gly Val Gln Cys Phe Ser Arg Tyr Pro Asp His Met
            420                 425                 430

Lys Gln His Asp Phe Phe Lys Ser Ala Met Pro Glu Gly Tyr Val Gln
        435                 440                 445

Glu Arg Thr Ile Phe Phe Lys Asp Asp Gly Asn Tyr Lys Thr Arg Ala
    450                 455                 460

Glu Val Lys Phe Glu Gly Asp Thr Leu Val Asn Arg Ile Glu Leu Lys
465                 470                 475                 480

Gly Ile Asp Phe Lys Glu Asp Gly Asn Ile Leu Gly His Lys Leu Glu
                485                 490                 495

Tyr Asn Tyr Asn Ser His Asn Val Tyr Ile Met Ala Asp Lys Gln Lys
            500                 505                 510

Asn Gly Ile Lys Val Asn Phe Lys Ile Arg His Asn Ile Glu Asp Gly
        515                 520                 525

Ser Val Gln Leu Ala Asp His Tyr Gln Gln Asn Thr Pro Ile Gly Asp
    530                 535                 540

Gly Pro Val Leu Leu Pro Asp Asn His Tyr Leu Ser Thr Gln Ser Ala
545                 550                 555                 560

Leu Ser Lys Asp Pro Asn Glu Lys Arg Asp His Met Val Leu Leu Glu
                565                 570                 575

Phe Val Thr Ala Ala Gly Ile Thr Leu Gly Met Asp Glu Leu Tyr Lys
            580                 585                 590
```

<210> SEQ ID NO 13
<211> LENGTH: 604
<212> TYPE: PRT
<213> ORGANISM: Artificial Sequence
<220> FEATURE:
<223> OTHER INFORMATION: MCH1R-linker-EGFP

<400> SEQUENCE: 13

```
Met Asp Leu Glu Ala Ser Leu Leu Pro Thr Gly Pro Asn Ala Ser Asn
  1               5                  10                  15
Thr Ser Asp Gly Pro Asp Asn Leu Thr Ser Ala Gly Ser Pro Pro Arg
             20                  25                  30
Thr Gly Ser Ile Ser Tyr Ile Asn Ile Ile Met Pro Ser Val Phe Gly
             35                  40                  45
Thr Ile Cys Leu Leu Gly Ile Ile Gly Asn Ser Thr Val Ile Phe Ala
         50                  55                  60
Val Val Lys Lys Ser Lys Leu His Trp Cys Asn Asn Val Pro Asp Ile
 65                  70                  75                  80
Phe Ile Ile Asn Leu Ser Val Val Asp Leu Leu Phe Leu Leu Gly Met
                 85                  90                  95
Pro Phe Met Ile His Gln Leu Met Gly Asn Gly Val Trp His Phe Gly
            100                 105                 110
Glu Thr Met Cys Thr Leu Ile Thr Ala Met Asp Ala Asn Ser Gln Phe
            115                 120                 125
Thr Ser Thr Tyr Ile Leu Thr Ala Met Ala Ile Asp Arg Tyr Leu Ala
        130                 135                 140
Thr Val His Pro Ile Ser Ser Thr Lys Phe Arg Lys Pro Ser Met Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Lys Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
        275                 280                 285
Phe Val Tyr Leu Tyr Asn Ala Ala Ile Ser Leu Gly Tyr Ala Asn Ser
    290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Thr
                325                 330                 335
Val Ser Asn Ala Gln Thr Ala Asp Glu Glu Arg Thr Glu Ser Lys Gly
            340                 345                 350
Thr Val Asp Gly Thr Ala Gly Pro Gly Ser Ile Ala Thr Met Val Ser
        355                 360                 365
Lys Gly Glu Glu Leu Phe Thr Gly Val Val Pro Ile Leu Val Glu Leu
    370                 375                 380
Asp Gly Asp Val Asn Gly His Lys Phe Ser Val Ser Gly Glu Gly Glu
385                 390                 395                 400
Gly Asp Ala Thr Tyr Gly Lys Leu Thr Leu Lys Phe Ile Cys Thr Thr
```

-continued

```
                      405                 410                 415
Gly Lys Leu Pro Val Pro Trp Pro Thr Leu Val Thr Leu Thr Tyr
            420                 425                 430

Gly Val Gln Cys Phe Ser Arg Tyr Pro Asp His Met Lys Gln His Asp
        435                 440                 445

Phe Phe Lys Ser Ala Met Pro Glu Gly Tyr Val Gln Glu Arg Thr Ile
    450                 455                 460

Phe Phe Lys Asp Asp Gly Asn Tyr Lys Thr Arg Ala Glu Val Lys Phe
465                 470                 475                 480

Glu Gly Asp Thr Leu Val Asn Arg Ile Glu Leu Lys Gly Ile Asp Phe
                485                 490                 495

Lys Glu Asp Gly Asn Ile Leu Gly His Lys Leu Glu Tyr Asn Tyr Asn
            500                 505                 510

Ser His Asn Val Tyr Ile Met Ala Asp Lys Gln Lys Asn Gly Ile Lys
        515                 520                 525

Val Asn Phe Lys Ile Arg His Asn Ile Glu Asp Gly Ser Val Gln Leu
    530                 535                 540

Ala Asp His Tyr Gln Gln Asn Thr Pro Ile Gly Asp Gly Pro Val Leu
545                 550                 555                 560

Leu Pro Asp Asn His Tyr Leu Ser Thr Gln Ser Ala Leu Ser Lys Asp
                565                 570                 575

Pro Asn Glu Lys Arg Asp His Met Val Leu Leu Glu Phe Val Thr Ala
            580                 585                 590

Ala Gly Ile Thr Leu Gly Met Asp Glu Leu Tyr Lys
        595                 600
```

<210> SEQ ID NO 14
<211> LENGTH: 673
<212> TYPE: PRT
<213> ORGANISM: Artificial Sequence
<220> FEATURE:
<223> OTHER INFORMATION: MCH1R-linker-EGFP

<400> SEQUENCE: 14

```
Met Ser Val Gly Ala Met Lys Lys Gly Val Gly Arg Ala Val Gly Leu
  1               5                  10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
        50                  55                  60

Thr Gly Thr Gly Trp Met Asp Leu Glu Ala Ser Leu Leu Pro Thr Gly
 65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile Met
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
    130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
```

-continued

```
                165                 170                 175
Val Trp His Phe Gly Glu Thr Met Cys Thr Leu Ile Thr Ala Met Asp
            180                 185                 190
Ala Asn Ser Gln Phe Thr Ser Thr Tyr Ile Leu Thr Ala Met Ala Ile
        195                 200                 205
Asp Arg Tyr Leu Ala Thr Val His Pro Ile Ser Ser Thr Lys Phe Arg
    210                 215                 220
Lys Pro Ser Met Ala Thr Leu Val Ile Cys Leu Leu Trp Ala Leu Ser
225                 230                 235                 240
Phe Ile Ser Ile Thr Pro Val Trp Leu Tyr Ala Arg Leu Ile Pro Phe
                245                 250                 255
Pro Gly Gly Ala Val Gly Cys Gly Ile Arg Leu Pro Asn Pro Asp Thr
            260                 265                 270
Asp Leu Tyr Trp Phe Thr Leu Tyr Gln Phe Phe Leu Ala Phe Ala Leu
        275                 280                 285
Pro Phe Val Val Ile Thr Ala Ala Tyr Val Lys Ile Leu Gln Arg Met
    290                 295                 300
Thr Ser Ser Val Ala Pro Ala Ser Gln Arg Ser Ile Arg Leu Arg Thr
305                 310                 315                 320
Lys Arg Val Thr Arg Thr Ala Ile Ala Ile Cys Leu Val Phe Phe Val
                325                 330                 335
Cys Trp Ala Pro Tyr Tyr Val Leu Gln Leu Thr Gln Leu Ser Ile Ser
            340                 345                 350
Arg Pro Thr Leu Thr Phe Val Tyr Leu Tyr Asn Ala Ala Ile Ser Leu
        355                 360                 365
Gly Tyr Ala Asn Ser Cys Leu Asn Pro Phe Val Tyr Ile Val Leu Cys
    370                 375                 380
Glu Thr Phe Arg Lys Arg Leu Val Leu Ser Val Lys Pro Ala Ala Gln
385                 390                 395                 400
Gly Gln Leu Arg Thr Val Ser Asn Ala Gln Thr Ala Asp Glu Glu Arg
                405                 410                 415
Thr Glu Ser Lys Gly Thr Val Asp Gly Thr Ala Gly Pro Gly Ser Ile
            420                 425                 430
Ala Thr Met Val Ser Lys Gly Glu Glu Leu Phe Thr Gly Val Val Pro
        435                 440                 445
Ile Leu Val Glu Leu Asp Gly Asp Val Asn Gly His Lys Phe Ser Val
    450                 455                 460
Ser Gly Glu Gly Glu Gly Asp Ala Thr Tyr Gly Lys Leu Thr Leu Lys
465                 470                 475                 480
Phe Ile Cys Thr Thr Gly Lys Leu Pro Val Pro Trp Pro Thr Leu Val
                485                 490                 495
Thr Thr Leu Thr Tyr Gly Val Gln Cys Phe Ser Arg Tyr Pro Asp His
            500                 505                 510
Met Lys Gln His Asp Phe Phe Lys Ser Ala Met Pro Glu Gly Tyr Val
        515                 520                 525
Gln Glu Arg Thr Ile Phe Phe Lys Asp Asp Gly Asn Tyr Lys Thr Arg
    530                 535                 540
Ala Glu Val Lys Phe Glu Gly Asp Thr Leu Val Asn Arg Ile Glu Leu
545                 550                 555                 560
Lys Gly Ile Asp Phe Lys Glu Asp Gly Asn Ile Leu Gly His Lys Leu
                565                 570                 575
Glu Tyr Asn Tyr Asn Ser His Asn Val Tyr Ile Met Ala Asp Lys Gln
            580                 585                 590
```

```
Lys Asn Gly Ile Lys Val Asn Phe Lys Ile Arg His Asn Ile Glu Asp
            595                 600                 605
Gly Ser Val Gln Leu Ala Asp His Tyr Gln Gln Asn Thr Pro Ile Gly
        610                 615                 620
Asp Gly Pro Val Leu Leu Pro Asp Asn His Tyr Leu Ser Thr Gln Ser
625                 630                 635                 640
Ala Leu Ser Lys Asp Pro Asn Glu Lys Arg Asp His Met Val Leu Leu
                645                 650                 655
Glu Phe Val Thr Ala Ala Gly Ile Thr Leu Gly Met Asp Glu Leu Tyr
            660                 665                 670
Lys

<210> SEQ ID NO 15
<211> LENGTH: 1269
<212> TYPE: DNA
<213> ORGANISM: Human

<400> SEQUENCE: 15
atgtcagtgg gagccatgaa gaagggagtg gggagggcag ttgggcttgg aggcggcagc      60
ggctgccagg ctacggagga agacccctt cccaactgcg gggcttgcgc tccgggacaa     120
ggtggcaggc gctggaggct gccgcagcct cgtgggtgg aggggagctc agctcggttg     180
tgggagcagg cgaccggcac tggctggatg acctggaag cctcgctgct gcccactggt     240
cccaacgcca gcaacacctc tgatggcccc gataacctca cttcggcagg atcacctcct     300
cgcacgggga gcatctccta catcaacatc atcatgcctt cggtgttcgg caccatctgc     360
ctcctgggca tcatcgggaa ctccacggtc atcttcgcgg tcgtgaagaa gtccaagctg     420
cactggtgca acaacgtccc cgacatcttc atcatcaacc tctcggtagt agatctcctc     480
tttctcctgg gcatgccctt catgatccac cagctcatgg gcaatgggt gtggcacttt     540
ggggagacca tgtgcacccc tcatcacggcc atggatgcca atagtcagtt caccagcacc     600
tacatcctga ccgccatggc cattgaccgc tacctggcca ctgtccaccc catctcttcc     660
acgaagttcc ggaagccctc tgtggccacc ctggtgatct gcctcctgtg ggcccctctcc     720
ttcatcagca tcaccctgt gtggctgtat gccagactca tccccttccc aggaggtgca     780
gtgggctgcg gcatacgcct gcccaaccca gacactgacc tctactggtt caccctgtac     840
cagttttttcc tggcctttgc cctgcctttt gtggtcatca cagccgcata cgtgaggatc     900
ctgcagcgca tgacgtcctc agtggccccc gcctcccagc gcagcatccg gctgcggaca     960
aagagggtga cccgcacagc catcgccatc gtcctggtct ctttgtgtg ctgggcaccc    1020
tactatgtgc tacagctgac ccagttgtcc atcagccgcc cgaccctcac ctttgtctac    1080
ttatacaatg cggccatcag cttgggctat gccaacagct gcctcaaccc ctttgtgtac    1140
atcgtgctct gtgagacgtt ccgcaaacgc ttggtcctgt cggtgaagcc tgcagcccag    1200
ggcagcttcg cgctgtcag caacgctcag acggctgacg aggagaggac agaaagcaaa    1260
ggcacctga                                                              1269

<210> SEQ ID NO 16
<211> LENGTH: 1062
<212> TYPE: DNA
<213> ORGANISM: Human

<400> SEQUENCE: 16
atggacctgg aagcctcgct gctgcccact ggtcccaatg ccagcaacac ctctgatggc      60
```

-continued

```
cccgataacc tcacttcggc aggatcacct cctcgcacgg ggagcatctc ctacatcaac      120
atcatcatgc cttcggtgtt cggcaccatc tgcctcctgg gcatcatcgg gaactccacg      180
gtcatcttcg cggtcgtgaa gaagtccaag ctgcactggt gcaacaacgt ccccgacatc      240
ttcatcatca acctctcggt agtagatctc ctctttctcc tgggcatgcc cttcatgatc      300
caccagctca tgggcaatgg ggtgtggcac tttggggaga ccatgtgcac cctcatcacg      360
gccatggatg ccaatagtca gttcaccagc acctacatcc tgaccgccat ggccattgac      420
cgctacctgg ccactgtcca ccccatctct tccacgaagt tccggaagcc ctctgtggcc      480
accctggtga tctgcctcct gtgggccctc tccttcatca gcatcacccc tgtgtggctg      540
tatgccagac tcatcccctt ccaggaggt gcagtgggct gcggcatacg cctgcccaac      600
ccagacactg acctctactg gttcaccctg taccagtttt tcctggcctt tgccctgcct      620
tttgtggtca tcacagccgc atacgtgagg atcctgcagc gcatgacgtc ctcagtggcc      720
cccgcctccc agcgcagcat ccggctgcgg acaaagaggg tgacccgcac agccatcgcc      780
atctgtctgg tcttctttgt gtgctgggca ccctactatg tgctacagct gacccagttg      840
tccatcagcc gcccgaccct caccttttgtc tacttataca atgcggccat cagcttgggc      900
tatgccaaca gctgcctcaa ccccttttgtg tacatcgtgc tctgtgagac gttccgcaaa      960
cgcttggtcc tgtcggtgaa gcctgcagcc caggggcagc ttcgcgctgt cagcaacgct     1020
cagacggctg acgaggagag gacagaaagc aaaggcacct ga                        1062
```

<210> SEQ ID NO 17
<211> LENGTH: 2080
<212> TYPE: DNA
<213> ORGANISM: Mouse
<220> FEATURE:
<221> NAME/KEY: misc_feature
<222> LOCATION: (1)...(2080)
<223> OTHER INFORMATION: n = A,T,C or G

<400> SEQUENCE: 17

```
ggcggtagag gaagaccctt ttctggactg cggggctcaa gctccggaca aggcggtgga       60
gggcgctgga ggctgccgca gcctgcgtgg gtggacgggc gctccactcc agggagcagg      120
cgacctgcac cggctgcatg gatctgcaag cctcgttgct gtccactggc cccaatgcca      180
gcaacatctc cgatggccag gataatttca cattggcggg gccacctcct cgcacaagga      240
gtgtctccta catcaacatc atcatgcctt cagtgtttgg taccatctgt ctcctgggca      300
ttgtgggaaa ctccacagtc attttttgccg tggtgaagaa atccaagctg cactggtgca      360
gcaacgtccc tgacatcttc atcatcaacc tctctgtggt ggatctgctt ttcctgctgg      420
gcatgccttt catgatccac cagctcatgg gtaatggtgt ctggcacttt ggggaaacca      480
tgtgcaccct catcacagcc atggacgcca acagtcagtt caccagcacc tacatcctga      540
ctgctatggc cattgaccgc tacttggcca ccgtccatcc catctcctcc accaagttcc      600
ggaagccctc catggccacc ctggtgatct gcctcctgtg ggctctctcg ttcattagca      660
tcactcctgt gtggctctat gccaggctta tccccttccc aggggtgct gtgggctgtg      720
gcatccgcct accaaaccca gatactgatc tttactggtt cactctgtat cagtttttcc      780
tggccttcgc ccttccgttt gtggtcatca ctgctgcgta cgtgaaaata ctacagcgca      840
tgacgtcttc ggtggcccca gcctctcaac gcagcatccg gcttcggaca aagagggtga      900
cccgcacagc cattgccatc tgtctggtct tctttgtgtg ctgggcgccc tactacgtgc      960
```

```
tgcagctgac ccagttgtcc atcagccgcc cgaccctcac attcgtctac ctgtacaatg       1020
cggccatcag cttgggctat gccaacagct gcctcaatcc ctttgtgtac atagtactct       1080
gtgagacctt tcgaaaacgc ttggtgctgt cggtgaagcc cgcggcccag gggcagcttc       1140
gcacggtcag caatgctcag acagctgacg aggagaggac agaaagcaaa ggcacctgac       1200 aatcccccc gggtcacctcc aagtcaggtc accgcatcaa accatgggga gagatactga       1260 gataaaccg gggctaccct gggaggatgc agaagctgga ggctggggc ttgtagcaaa         1320 ccacattcca cggggcccac aaattgctag ggaggcttgc agcctggttt ggggggaag        1380 cctcagactg cagggatccc cttgacagaa tagaagcgga gcaagaagga aagggtggtt       1440
tgactggttc tcggggtctg tatctgttgg ctcgcatata tctttctctc aagggaagaa       1500
ggcggaggtg cctagctggg ttcctttaaa actaggcagg gctaggatct gagcagctag       1560
ggctctactg tgagactggg caagccgagc gttccctccc atctctcatt ggtgttgata       1620
gaaggcagtc tttctcccaa gctggtggat ctcctgaagc acgctgcctg ggctccagca       1680
tcctgtgcgg atttcacgtt ctctttaggg gatgcatgtt gacactgggg tgtgggctct       1740
gagcccacag gagtttaaaa aaccaaaaga gctcagagtg tcgagagaga cccaatcacc       1800
gagaatgaca aggcaacctg gggtggatgt ggatcttgaa actaataaaa aggggttttc       1860
acagtgacag cgacattctc ttcatagggc acagctgtca gtctatggct gatccagagc       1920
gagcatccat gaattctgca tgtgcagggg tcactctaat acctgatatg ttggcatcat       1980
ctttgtgctt gagccttccn ctcccaaatg ggaatgaaat aaaggcaaat tcccncccc        2040 cccaaaaaag gggnaaaaaa aaaaaaaaaa aaaaaaaaa                             2080
```

<210> SEQ ID NO 18
<211> LENGTH: 3357
<212> TYPE: DNA
<213> ORGANISM: Mouse
<220> FEATURE:
<221> NAME/KEY: misc_feature
<222> LOCATION: (1)...(3357)
<223> OTHER INFORMATION: n = A,T,C or G

<400> SEQUENCE: 18

```
ggcggtagag gaagacccctt ttctggactg cggggctcaa gctccggaca aggcggtgga       60
gggcgctgga ggctgccgca gcctgcgtgg gtggacgggc gctccactcc agggagcagg       120
cgacctgcac cggctgcatg gatctgcaag cctcgttgct gtccactggc cccaatgcca       180
gcaacatctc cgatggccag gataatttca cattggcggg tgagtcgagt tggagtcctc       240
cctcctccgg gatgggtgtg gaaaatggga aggtttcacc tcccaagcca aactgcctgg       300
gaaactttat cttacagttc ttggtgataa gatctgcagt cggctttgcc tgaagaggaa       360
gaggagagga ggggacacca gctaggacag aaggggcagg gaggaataga gatggggcag       420
aggcacattt agaaacaaca agggttggtg acaagacgtg aggcaggctt gaggggaaag       480
cttgctgatg agtcccaaat atgctttgca gggggggggg ggggggaatc aaggctggag       540
aagcaagcaa gcaagacagc aagacagcgg gcggtagta tgtgggagcc agcagaagcg       600
ctttgattca ccgctatcct gggctcaatc ctctggcctc gcactgggga atgggtct        660 gagtggtcct tgctgtcttc tggcaaaggc tgctgggagc aaaagacttc acagggcgtg       720
agaggattaa cttttctggt gaattaagct tcttgacatt tgcagaacgt caatgcctta       780
aaattctagc tctgaaggag aagggaatga agggaaaga gggaaggttg gtgtggagaa        840
attcccaagc ttctggggtg taacacagct ccagtcccta ccctattggg aaagcccaga       900
```

```
ctcaggagac atggtccaag gaaatccctg acagaaaacc gggagagggc agggctgtgg      960
agcctgaaac acaccccaca cccatggtga cagtcacttc tcacatatgc ctaggaacct     1020
atctgaaacc tttggccatc tctctctgaa aagatgaggc tgcaaataca cacacacaca     1080
cacacacaca cacacacaca cacacacaca cacacacaca cacacacaca aatgtccttc     1140
aagcctttt  gacaaggttt tctggtggat cccggggata tgaagttgtt ctcagcagat     1200
atctgggagt cttgactcct ggccctctga gtaaatggat gaagcgaaga agaatggggt     1260
cctctgagta acaggtggat ctagaaaatc ctataggagt caccagggca cggtggagga     1320
gggtaaggta cagaactaac aatagcccga aaggggaaa  cagcaggaga tgattccaga     1380
gacgtagtga ccccaagctg caagggaaag catgaggggc cagcaggaag ccgacatgg      1440
caggttgtca gcttctagat cggaaggcgg gtcacacttg ctctttctat cctcagggcc     1500
acctcctcgc acaaggagtg tctcctacat caacatcatc atgccttcag tgtttggtac     1560
catctgtctc ctgggcattg tgggaaactc cacagtcatt tttgccgtgg tgaagaaatc     1620
caagctgcac tggtgcagca acgtccctga catcttcatc atcaacctct ctgtggtgga     1680
tctgcttttc ctgctgggca tgcctttcat gatccaccag ctcatgggta atggtgtctg     1740
gcactttggg gaaaccatgt gcaccctcat cacagccatg gacgccaaca gtcagttcac     1800
cagcacctac atcctgactg ctatggccat tgaccgctac ttggccaccg tccatcccat     1860
ctcctccacc aagttccgga gccctccat  ggccaccctg gtgatctgcc tcctgtgggc     1920
tctctcgttc attagcatca ctcctgtgtg gctctatgcc aggcttatcc ccttcccagg     1980
gggtgctgtg ggctgtggca tccgcctacc aaacccagat actgatcttt actggttcac     2040
tctgtatcag ttttttcctgg ccttcgccct tccgtttgtg gtcatcactg ctgcgtacgt     2100
gaaaatacta cagcgcatga cgtcttcggt ggcccagcc  tctcaacgca gcatccggct     2160
tcggacaaag agggtgaccc gcacagccat tgccatctgt ctggtcttct ttgtgtgctg     2220
ggcgccctac tacgtgctgc agctgaccca gttgtccatc agccgcccga ccctcacatt     2280
cgtctacctg tacaatgcgg ccatcagctt gggctatgcc aacagctgcc tcaatccctt     2340
tgtgtacata gtactctgtg agaccttcg  aaaacgcttg gtgctgtcgg tgaagcccgc     2400
ggcccagggg cagcttcgca cggtcagcaa tgctcagaca gctgacgagg agaggacaga     2460
aagcaaaggc acctgacaat cccccccggt cacctccaag tcaggtcacc gcatcaaacc     2520
atggggagag atactgagat aaaccccgggg ctaccctggg aggatgcaga agctggaggc     2580
tgggggcttg tagcaaacca cattccacgg ggcccacaaa ttgctaggga ggcttgcagc     2640
ctggtttggg ggggaagcct cagactgcag ggatccccctt gacagaatag aagcggagca     2700
agaaggaaag ggtggtttga ctggttctcg gggtctgtat ctgttggctc gcatatatct     2760
ttctctcaag ggaagaaggc ggaggtgcct agctgggttc cttaaaaact aggcagggct     2820
aggatctgag cagctagggc tctactgtga gactgggcaa gccgagcgtt ccctcccatc     2880
tctcattggt gttgatagaa ggcagtctt  ctcccaagct ggtggatctc ctgaagcacg     2940
ctgcctgggc tccagcatcc tgtgcggatt tcacgttctc tttaggggat gcatgttgac     3000
actgggtgt  gggctctgag cccacaggag tttaaaaaac caaaagagct cagagtgtcg     3060
agagagaccc aatcaccgag aatgacaagg caacctgggg tggatgtgga tcttgaaact     3120
aataaaaagg ggttttcaca gtgacagcga cattctcttc ataggcaca  gctgtcagtc     3180
tatggctgat ccagagcgag catccatgaa ttctgcatgt gcagggtca  ctctaatacc     3240
```

```
tgatatgttg gcatcatctt tgtgcttgag ccttccnctc ccaaatggga atgaaataaa      3300
ggcaaattcc cnccccccc aaaaagggg naaaaaaaa aaaaaaaaa aaaaaaa             3357

<210> SEQ ID NO 19
<211> LENGTH: 1062
<212> TYPE: DNA
<213> ORGANISM: Artificial Sequence
<220> FEATURE:
<223> OTHER INFORMATION: Human short form/mouse species chimeric MCH1R

<400> SEQUENCE: 19
atggacctgg aagcctcgct gctgcccact ggtcccaatg ccagcaacac ctctgatggc       60
cccgataacc tcacttcggc aggatcacct cctcgcacgg ggagcatctc ctacatcaac      120
atcatcatgc cttcggtgtt cggcaccatc tgcctcctgg gcatcatcgg gaactccacg      180
gtcatcttcg cggtcgtgaa gaagtccaag ctgcactggt gcaacaacgt ccccgacatc      240
ttcatcatca acctctcggt agtagatctc ctctttctcc tggcatgcc cttcatgatc       300 caccagctca tgggcaatgg ggtgtggcac tttggggaga ccatgtgcac cctcatcacg      360
gccatggatg ccaatagtca gttcaccagc acctacatcc tgaccgccat ggccattgac      420
cgctacctgg ccactgtcca ccccatctct tccacgaagt tccggaagcc ctccatggcc      480
accctggtga tctgcctcct gtgggctctc tcgttcatta gcatcactcc tgtgtggctc      540
tatgccaggc ttatcccctt cccaggggt gctgtgggct gtggcatccg cctaccaaac       600
ccagatactg atctttactg gttcactctg tatcagtttt tcctggcctt cgcccttccg      660
tttgtggtca tcactgctgc gtacgtgaaa atactacagc gcatgacgtc ttcggtggcc      720
ccagcctctc aacgcagcat ccggcttcgg acaaagaggg tgaccgcac agccattgcc       780 atctgtctgg tcttctttgt gtgctgggcg ccctactacg tgctgcagct gacccagttg      840
tccatcagcc gcccgaccct cacattcgtc tacctgtaca atgcggccat cagcttgggc      900
tatgccaaca gctgcctcaa tccctttgtg tacatagtac tctgtgagac ctttcgaaaa      960
cgcttggtgc tgtcggtgaa gcccgcggcc caggggcagc ttcgcacggt cagcaatgct     1020
cagacagctg acgaggagag gacagaaagc aaaggcacct ga                        1062

<210> SEQ ID NO 20
<211> LENGTH: 1269
<212> TYPE: DNA
<213> ORGANISM: Artificial Sequence
<220> FEATURE:
<223> OTHER INFORMATION: Human long form/mouse species chimeric MCH1R

<400> SEQUENCE: 20
atgtcagtgg gagccatgaa gaagggagtg gggagggcag ttgggcttgg aggcggcagc       60
ggctgccagg ctacggagga agacccctt cccaactgcg gggcttgcgc tccgggacaa       120
ggtggcaggc gctggaggct gccgcagcct gcgtgggtgg aggggagctc agctcggttg      180
tgggagcagg cgaccggcac tggctggatg gacctggaag cctcgctgct gcccactggt      240
cccaacgcca gcaacacctc tgatggcccc gataacctca cttcggcagg atcacctcct      300
cgcacgggga gcatctccta catcaacatc atcatgcctt cggtgttcgg caccatctgc      360
ctcctgggca tcatcgggaa ctccacggtc atcttcgcgg tcgtgaagaa gtccaagctg      420
cactggtgca acaacgtccc cgacatcttc atcatcaacc tctcggtagt agatctcctc      480
tttctcctgg gcatgccctt catgatccac cagctcatgg gcaatggggt gtggcacttt      540
ggggagacca tgtgcaccct catcacggcc atggatgcca atagtcagtt caccagcacc      600
```

-continued

```
tacatcctga ccgccatggc cattgaccgc tacctggcca ctgtccaccc catctcttcc      660
acgaagttcc ggaagccctc catggccacc ctggtgatct gcctcctgtg ggctctctcg      720
ttcattagca tcactcctgt gtggctctat gccaggctta tcccctttcc aggggggtgct     780 gtgggctgtg catccgcct accaaaccca gatactgatc tttactggtt cactctgtat       840 cagttttttcc tggccttcgc ccttccgttt gtggtcatca ctgctgcgta cgtgaaaata    900
ctacagcgca tgacgtcttc ggtggcccca gcctctcaac gcagcatccg gcttcggaca     960
aagagggtga cccgcacagc cattgccatc tgtctggtct tctttgtgtg ctgggcgccc     1020
tactacgtgc tgcagctgac ccagttgtcc atcagccgcc cgaccctcac attcgtctac    1080
ctgtacaatg cggccatcag cttgggctat gccaacagct gcctcaatcc ctttgtgtac    1140
atagtactct gtgagacctt tcgaaaacgc ttggtgctgt cggtgaagcc cgcggcccag    1200
gggcagcttc gcacggtcag caatgctcag acagctgacg aggagaggac agaaagcaaa    1260
ggcacctga                                                              1269

<210> SEQ ID NO 21
<211> LENGTH: 966
<212> TYPE: DNA
<213> ORGANISM: Aequorea Victoria

<400> SEQUENCE: 21
tacacacgaa taaagataa caaagatgag taaaggagaa gaacttttca ctggagttgt       60
cccaattctt gttgaattag atggtgatgt taatgggcac aaattttctg tcagtggaga     120
gggtgaaggt gatgcaacat acggaaaact taccctaaaa tttatttgca ctactggaaa    180
actacctgtt ccatggccaa cacttgtcac tactttctct tatggtgttc aatgcttttc    240
aagataccca gatcatatga aacagcatga ctttttcaag agtgccatgc ccgaaggtta    300
tgtacaggaa agaactatat tttcaaaga tgacgggaac tacaagacac gtgctgaagt    360
caagtttgaa ggtgataccc ttgttaatag aatcgagtta aaaggtattg attttaaaga    420
agatggaaac attcttggac acaaattgga atacaactat aactcacaca atgtatacat    480
catggcagac aaacaaaaga atggaatcaa agttaacttc aaaattagac acaacattga    540
agatggaagc gttcaactag cagaccatta tcaacaaaat actccaattg gcgatggccc    600 tgtccttttta ccagacaacc attacctgtc cacacaatct gccctttcga agatcccaa    660 cgaaaagaga gaccacatgg tccttcttga gtttgtaaca gctgctggga ttacacatgg    720
catggatgaa ctatacaaat aaatgtccag acttccaatt gacactaaag tgtccgaaca    780
attactaaaa tctcagggtt cctggttaaa ttcaggctga gatattattt atatatttat    840
agattcatta aaattgtatg aataaattat tgatgttatt gatagaggtt attttcttat    900
taaacaggct acttggagtg tattcttaat tctatattaa ttacaatttg atttgacttg    960
ctcaaa                                                                966

<210> SEQ ID NO 22
<211> LENGTH: 765
<212> TYPE: DNA
<213> ORGANISM: Artificial Sequence
<220> FEATURE:
<223> OTHER INFORMATION: GFP derivative

<400> SEQUENCE: 22
gtcgacggta ccgcgggccc gggatccatc gccaccatgg tgagcaaggg cgaggagctg      60
```

-continued

```
ttcaccgggg tggtgcccat cctggtcgag ctggacggcg acgtaaacgg ccacaagttc      120
agcgtgtccg gcgagggcga gggcgatgcc acctacggca agctgaccct gaagttcatc      180
tgcaccaccg gcaagctgcc cgtgccctgg cccacccctcg tgaccaccct gacctacggc      240
gtgcagtgct tcagccgcta ccccgaccac atgaagcagc acgacttctt caagtccgcc      300
atgcccgaag gctacgtcca ggagcgcacc atcttcttca aggacgacgg caactacaag      360
acccgcgccg aggtgaagtt cgaggcgac accctggtga accgcatcga gctgaagggc      420
atcgacttca aggaggacgg caacatcctg ggcacaagc tggagtacaa ctacaacagc      480
cacaacgtct atatcatggc cgacaagcag aagaacggca tcaaggtgaa cttcaagatc      540
cgccacaaca tcgaggacgg cagcgtgcag ctcgccgacc actaccagca gaacaccccc      600
atcggcgacg ccccgtgct gctgcccgac aaccactacc tgagcaccca gtccgccctg      660
agcaaagacc ccaacgagaa gcgcgatcac atggtcctgc tggagttcgt gaccgccgcc      720
gggatcactc tcggcatgga cgagctgtac aagtaaagcg ccgc                      765
```

<210> SEQ ID NO 23
<211> LENGTH: 720
<212> TYPE: DNA
<213> ORGANISM: Artificial Sequence
<220> FEATURE:
<223> OTHER INFORMATION: GFP derivative

<400> SEQUENCE: 23

```
atggtgagca agggcgagga gctgttcacc ggggtggtgc ccatcctggt cgagctggac       60
ggcgacgtaa acgccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttgaccta cggcgtgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaag gtctatatca ccgccgacaa gcagaagaac      480
ggcatcaagg tgaacttcaa gacccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

<210> SEQ ID NO 24
<211> LENGTH: 720
<212> TYPE: DNA
<213> ORGANISM: Artificial Sequence
<220> FEATURE:
<223> OTHER INFORMATION: GFP derivative

<400> SEQUENCE: 24

```
atggtgagca agggcgagga gctgttcacc ggggtggtgc ccatcctggt cgagctggac       60
ggcgacgtaa acgccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcggcta cggcgtgcag tgcttcgccc gctaccccga ccacatgcgc      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
```

```
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaagtaa      720

<210> SEQ ID NO 25
<211> LENGTH: 720
<212> TYPE: DNA
<213> ORGANISM: Artificial Sequence
<220> FEATURE:
<223> OTHER INFORMATION: GFP derivative

<400> SEQUENCE: 25
atggtgagca agggcgagga gctgttcacc ggggtggtgc ccatcctggt cgagctggac       60
ggcgacgtaa acggccacag gttcagcgtg tccggcgagg gcgagggcga tgccacctac      120
ggcaagctga ccctgaagtt catctgcacc accggcaagc tgcccgtgcc ctggcccacc      180
ctcgtgacca ccctgacctg gggcgtgcag tgcttcagcc gctacccgca ccacatgaag      240
cagcacgact tcttcaagtc cgccatgccc gaaggctacg tccaggagcg taccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacat cagccacaac gtctatatca ccgccgacaa gcagaagaac      480
ggcatcaagg cccacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720

<210> SEQ ID NO 26
<211> LENGTH: 3092
<212> TYPE: DNA
<213> ORGANISM: Artificial Sequence
<220> FEATURE:
<223> OTHER INFORMATION: Mouse MCH1R-linker-EGFP

<400> SEQUENCE: 26
atggatctgc aagcctcgtt gctgtccact ggccccaatg ccagcaacat ctccgatggc       60
caggataatt tcacattggc gggtgagtcg agttggagtc ctccctcctc cgggatgggt      120
gtggaaaatg ggaaggtttc acctcccaag ccaaactgcc tgggaaactt tatcttacag      180
ttcttggtga taagatctgc agtcggcttt gcctgaagag gaagaggaga ggagggggaca      240 ccagctagga cagaaggggc aggaggaat agagatgggg cagaggcaca tttagaaaca      300
acaagggttg gtgacaagac gtgaggcagg cttgagggga aagcttgctg atgagtccca      360
aatatgcttt gcaggggggg ggggggggga atcaaggctg gagaagcaag caagcaagac      420
agcaagacag cggcgggta gtatgtggga gccagcagaa gcgctttgat tcaccgctat      480
cctgggctca atcctctggc ctcgcactgg ggaaatgggg tctgagtggt ccttgctgtc      540
ttctggcaaa ggctgctggg agcaaaagac ttcacagggc gtgagaggat taactttcct      600
ggtgaattaa gcttcttgac atttgcagaa cgtcaatgcc ttaaaattct agctctgaag      660
```

```
gagaagggaa tgaagggaa agagggaagg ttggtgtgga gaaattccca agcttctggg      720
gtgtaacaca gctccagtcc ctaccctatt gggaaagccc agactcagga gacatggtcc      780
aaggaaatcc ctgacagaaa accgggagag ggcagggctg tggagcctga acacacccc       840 acacccatgg tgacagtcac ttctcacata tgcctaggaa cctatctgaa acctttggcc      900
atctctctct gaaagatga ggctgcaaat acacacacac acacacacac acacacacac       960
acacacacac acacacacac acacacacac acaaatgtcc ttcaagcctt tttgacaagg     1020
ttttctggtg gatcccgggg atatgaagtt gttctcagca gatatctggg agtcttgact     1080
cctggccctc tgagtaaatg gatgaagcga agaagaatgg ggtcctctga gtaacaggtg     1140
gatctagaaa atcctatagg agtcaccagg gcacggtgga ggagggtaag gtacagaact     1200
aacaatagcc cgagaagggg aaacagcagg agatgattcc agagacgtag tgaccccaag     1260
ctgcaaggga aagcatgagg ggccagcagg aaggccgaca tggcaggttg tcagcttcta     1320
gatcggaagg cgggtcacac ttgctctttc tatcctcagg gccacctcct cgcacaagga     1380
gtgtctccta catcaacatc atcatgcctt cagtgtttgg taccatctgt ctcctgggca     1440
ttgtgggaaa ctccacagtc attttttgccg tggtgaagaa atccaagctg cactggtgca     1500
gcaacgtccc tgacatcttc atcatcaacc tctctgtggt ggatctgctt ttcctgctgg     1560
gcatgccttt catgatccac cagctcatgg gtaatggtgt ctggcacttt ggggaaacca     1620
tgtgcaccct catcacagcc atggacgcca acagtcagtt caccagcacc tacatcctga     1680
ctgctatggc cattgaccgc tacttggcca ccgtccatcc catctcctcc accaagttcc     1740
ggaagccctc catggccacc ctggtgatct gcctcctgtg ggctctctcg ttcattagca     1800
tcactcctgt gtggctctat gccaggctta tccccttccc aggggtgct gtgggctgtg      1860 gcatccgcct accaaaccca gatactgatc tttactggtt cactctgtat cagttttttcc    1920 tggccttcgc ccttccgttt gtggtcatca ctgctgcgta cgtgaaaata ctacagcgca     1980
tgacgtcttc ggtggcccca gcctctcaac gcagcatccg gcttcggaca aagagggtga     2040
cccgcacagc cattgccatc tgtctggtct cttttgtgtg ctgggcgccc tactacgtgc     2100
tgcagctgac ccagttgtcc atcagccgcc cgaccctcac attcgtctac ctgtacaatg     2160
cggccatcag cttgggctat gccaacagct gcctcaatcc ctttgtgtac atagtactct     2220
gtgagacctt tcgaaaacgc ttggtgctgt cggtgaagcc cgcggcccag gggcagcttc     2280
gcacggtcag caatgctcag acagctgacg aggagaggac agaaagcaaa ggcaccgtcg     2340
acggtaccgc gggcccggga tccatcgcca ccatggtgag caagggcgag gagctgttca     2400
ccggggtggt gcccatcctg gtcgagctgg acggcgacgt aaacggccac aagttcagcg     2460
tgtccggcga gggcgagggc gatgccacct acggcaagct gaccctgaag ttcatctgca     2520
ccaccggcaa gctgcccgtg ccctggccca ccctcgtgac cacctgacc tacggcgtgc      2580 agtgcttcag ccgctacccc gaccacatga agcagcacga cttcttcaag tccgccatgc     2640
ccgaaggcta cgtccaggag cgcaccatct tcttcaagga cgacggcaac tacaagcccc    2700
gcgccgaggt gaagttcgag ggcgacaccc tggtgaaccg catcgagctg aagggcacg      2760 acttcaagga ggacggcaac atcctggggc acaagctgga gtacaactac aacagccaa     2820 acgtctatat catggccgac aagcagaaga acggcatcaa ggtgaacttc aagatccgcc     2880
acaacatcga ggacggcagc gtgcagctcg ccgaccacta ccagcagaac ccccccatcg     2940
gcgacggccc cgtgctgctg cccgacaacc actacctgag cacccagtcc gccctgagca     3000 aagacccaa cgagaagcgc gatcacatgg tcctgctgga gttcgtgacc gccgccggga     3060
```

-continued tcactctcgg catggacgag ctgtacaagt aa          3092

<210> SEQ ID NO 27
<211> LENGTH: 3056
<212> TYPE: DNA
<213> ORGANISM: Artificial Sequence
<220> FEATURE:
<223> OTHER INFORMATION: Mouse MCH1R/EGFP direct fusion

<400> SEQUENCE: 27

| | | |
|---|---|---|
| atggatctgc aagcctcgtt gctgtccact ggccccaatg ccagcaacat ctccgatggc | 60 |
| caggataatt tcacattggc gggtgagtcg agttggagtc ctccctcctc cgggatgggt | 120 |
| gtggaaaatg ggaaggtttc acctcccaag ccaaactgcc tgggaaactt tatcttacag | 180 |
| ttcttggtga taagatctgc agtcggcttt gcctgaagag gaagaggaga ggagggaca | 240 |
| ccagctagga cagaagggc agggaggaat agagatgggg cagaggcaca tttagaaaca | 300 |
| acaaggggttg gtgacaagac gtgaggcagg cttgagggga aagcttgctg atgagtccca | 360 |
| aatatgcttt gcaggggggg ggggggggga atcaaggctg gagaagcaag caagcaagac | 420 |
| agcaagacag cgggcgggta gtatgtggga gccagcagaa gcgctttgat tcaccgctat | 480 |
| cctgggctca atcctctggc ctcgcactgg ggaaatgggg tctgagtggt ccttgctgtc | 540 |
| ttctggcaaa ggctgctggg agcaaaagac ttcacagggc gtgagaggat taacttttct | 600 |
| ggtgaattaa gcttcttgac atttgcagaa cgtcaatgcc ttaaaattct agctctgaag | 660 |
| gagaagggaa tgaaggggaa agagggaagg ttggtgtgga gaaattccca agcttctggg | 720 |
| gtgtaacaca gctccagtcc ctaccctatt gggaagccc agactcagga gacatggtcc | 780 |
| aaggaaatcc ctgacagaaa accgggagag ggcagggctg tggagcctga acacacccc | 840 |
| acacccatgg tgacagtcac ttctcacata tgcctaggaa cctatctgaa acctttggcc | 900 |
| atctctctct gaaagatga ggctgcaaat acacacacac acacacacac acacacacac | 960 |
| acacacacac acacacacac acacacacac acaaatgtcc ttcaagcctt tttgacaagg | 1020 |
| ttttctggtg gatcccgggg atatgaagtt gttctcagca gatatctggg agtcttgact | 1080 |
| cctggccctc tgagtaaatg gatgaagcga agaagaatgg ggtcctctga gtaacaggtg | 1140 |
| gatctagaaa atcctatagg agtcaccagg gcacggtgga ggagggtaag gtacagaact | 1200 |
| aacaatagcc cgagaagggg aaacagcagg agatgattcc agagacgtag tgaccccaag | 1260 |
| ctgcaaggga agcatgagg ggccagcagg aaggccgaca tggcaggttg tcagcttcta | 1320 |
| gatcggaagg cgggtcacac ttgctctttc tatcctcagg gccacctcct cgcacaagga | 1380 |
| gtgtctccta catcaacatc atcatgcctt cagtgttgg taccatctgt ctcctgggca | 1440 |
| ttgtgggaaa ctccacagtc attttgccg tggtgaagaa atccaagctg cactggtgca | 1500 |
| gcaacgtccc tgcatcttc atcatcaacc tctctgtggt ggatctgctt ttcctgctgg | 1560 |
| gcatgccttt catgatccac cagctcatgg gtaatggtgt ctggcacttt ggggaaacca | 1620 |
| tgtgcaccct catcacagcc atggacgcca acagtcagtt caccagcacc tacatcctga | 1680 |
| ctgctatggc cattgaccgc tacttggcca ccgtccatcc catctcctcc accaagttcc | 1740 |
| ggaagccctc catggccacc ctggtgatct gcctcctgtg gctctctcg ttcattagca | 1800 |
| tcactcctgt gtggctctat gccaggctta tcccttccc aggggtgct gtgggctgtg | 1860 |
| gcatccgcct accaaaccca gatactgatc tttactggtt cactctgtat cagttttttcc | 1920 |
| tggccttcgc ccttccgttt gtggtcatca ctgctgcgta cgtgaaaata ctacagcgca | 1980 |

-continued

```
tgacgtcttc ggtggcccca gcctctcaac gcagcatccg gcttcggaca aagagggtga      2040
cccgcacagc cattgccatc tgtctggtct tctttgtgtg ctgggcgccc tactacgtgc      2100
tgcagctgac ccagttgtcc atcagccgcc cgaccctcac attcgtctac ctgtacaatg      2160
cggccatcag cttgggctat gccaacagct gcctcaatcc ctttgtgtac atagtactct      2220
gtgagacctt tcgaaaacgc ttggtgctgt cggtgaagcc cgcggcccag gggcagcttc      2280
gcacggtcag caatgctcag acagctgacg aggagaggac agaaagcaaa ggcaccatgg      2340
tgagcaaggg cgaggagctg ttcaccgggg tggtgcccat cctggtcgag ctggacggcg      2400
acgtaaacgg ccacaagttc agcgtgtccg gcgagggcga gggcgatgcc acctacggca      2460
agctgaccct gaagttcatc tgcaccaccg gcaagctgcc cgtgccctgg cccaccctcg      2520
tgaccaccct gacctacggc gtgcagtgct tcagccgcta ccccgaccac atgaagcagc      2580
acgacttctt caagtccgcc atgcccgaag gctacgtcca ggagcgcacc atcttcttca      2640
aggacgacgg caactacaag acccgcgccg aggtgaagtt cgagggcgac accctggtga      2700
accgcatcga gctgaagggc atcgacttca aggaggacgg caacatcctg ggcacaagc      2760 tggagtacaa ctacaacagc cacaacgtct atatcatggc cgacaagcag aagaacggca      2820
tcaaggtgaa cttcaagatc cgccacaaca tcgaggacgg cagcgtgcag ctcgccgacc      2880
actaccagca gaacaccccc atcggcgacg gccccgtgct gctgcccgac aaccactacc      2940
tgagcaccca gtccgccctg agcaaagacc ccaacgagaa gcgcgatcac atggtcctgc      3000
tggagttcgt gaccgccgcc gggatcactc tcggcatgga cgagctgtac aagtaa        3056
```

<210> SEQ ID NO 28
<211> LENGTH: 1815
<212> TYPE: DNA
<213> ORGANISM: Artificial Sequence
<220> FEATURE:
<223> OTHER INFORMATION: Human short form/mouse species chimeric
      MCH1R-linker-EGFP

<400> SEQUENCE: 28

```
atggacctgg aagcctcgct gctgcccact ggtcccaatg ccagcaacac ctctgatggc       60
cccgataacc tcacttcggc aggatcacct cctcgcacgg ggagcatctc ctacatcaac      120
atcatcatgc cttcggtgtt cggcaccatc tgcctcctgg gcatcatcgg gaactccacg      180
gtcatcttcg cggtcgtgaa gaagtccaag ctgcactggt gcaacaacgt ccccgacatc      240
ttcatcatca acctctcggt agtagatctc ctctttctcc tggcatgcc cttcatgatc      300 caccagctca tgggcaatgg ggtgtggcac tttggggaga ccatgtgcac cctcatcacg      360
gccatggatg ccaatagtca gttccaccag acctacatcc tgaccgccat ggccattgac      420
cgctacctgg ccactgtcca ccccatctct tccacgaagt tccggaagcc ctccatggcc      480
accctggtga tctgcctcct gtgggctctc tcgttcatta gcatcactcc tgtgtggctc      540
tatgccaggc ttatcccctt cccagggggt gctgtgggct gtggcatccg cctaccaaac      600
ccagatactg atctttactg gttcactctg tatcagtttt tcctggcctt cgcccttccg      660
tttgtggtca tcactgctgc gtacgtgaaa atactacagc gcatgacgtc ttcggtggcc      720
ccagcctctc aacgcagcat ccggcttcgg acaaagaggg tgaccgcac agccattgcc      780 atctgtctgg tcttctttgt gtgctgggcg ccctactacg tgctgcagct gacccagttg      840
tccatcagcc gccgaccct cacattcgtc tacctgtaca atgcggccat cagcttgggc      900
tatgccaaca gctgcctcaa tccctttgtg tacatagtac tctgtgagac ctttcgaaaa      960
```

-continued

| | |
|---|---|
| cgcttggtgc tgtcggtgaa gcccgcggcc caggggcagc ttcgcacggt cagcaatgct | 1020 |
| cagacagctg acgaggagag gacagaaagc aaaggcaccg tcgacggtac cgcgggcccg | 1080 |
| ggatccatcg ccaccatggt gagcaagggc gaggagctgt tcaccggggt ggtgcccatc | 1140 |
| ctggtcgagc tggacggcga cgtaaacggc cacaagttca gcgtgtccgg cgagggcgag | 1200 |
| ggcgatgcca cctacggcaa gctgaccctg aagttcatct gcaccaccgg caagctgccc | 1260 |
| gtgccctggc ccaccctcgt gaccaccctg acctacggcg tgcagtgctt cagccgctac | 1320 |
| cccgaccaca tgaagcagca cgacttcttc aagtccgcca tgcccgaagg ctacgtccag | 1380 |
| gagcgcacca tcttcttcaa ggacgacggc aactacaaga cccgcgccga ggtgaagttc | 1440 |
| gagggcgaca cccctggtgaa ccgcatcgag ctgaagggca tcgacttcaa ggaggacggc | 1500 |
| aacatcctgg ggcacaagct ggagtacaac tacaacagcc acaacgtcta tatcatggcc | 1560 |
| gacaagcaga agaacggcat caaggtgaac ttcaagatcc gccacaacat cgaggacggc | 1620 |
| agcgtgcagc tcgccgacca ctaccagcag aacacccca tcggcgacgg ccccgtgctg | 1680 |
| ctgcccgaca accactacct gagcacccag tccgccctga gcaaagaccc caacgagaag | 1740 |
| cgcgatcaca tggtcctgct ggagttcgtg accgccgccg ggatcactct cggcatggac | 1800 |
| gagctgtaca agtaa | 1815 |

<210> SEQ ID NO 29
<211> LENGTH: 2022
<212> TYPE: DNA
<213> ORGANISM: Artificial Sequence
<220> FEATURE:
<223> OTHER INFORMATION: Human long form/mouse species chimeric MCH1R-linker-EGFP

<400> SEQUENCE: 29

| | |
|---|---|
| atgtcagtgg gagccatgaa gaagggagtg gggagggcag ttgggcttgg aggcggcagc | 60 |
| ggctgccagg ctacggagga agaccccctt cccaactgcg gggcttgcgc tccgggacaa | 120 |
| ggtggcaggc gctggaggct gccgcagcct gcgtgggtgg aggggagctc agctcggttg | 180 |
| tgggagcagg cgaccggcac tggctggatg gacctggaag cctcgctgct gcccactggt | 240 |
| cccaacgcca gcaacaccctc tgatggcccc gataacctca cttcggcagg atcacctcct | 300 |
| cgcacgggga gcatctccta catcaacatc atcatgcctt cggtgttcgg caccatctgc | 360 |
| ctcctgggca tcatcgggaa ctccacggtc atcttcgcgg tcgtgaagaa gtccaagctg | 420 |
| cactggtgca acaacgtccc cgacatcttc atcatcaacc tctcggtagt agatctcctc | 480 |
| tttctcctgg gcatgccctt catgatccac cagctcatgg gcaatggggt gtggcacttt | 540 |
| ggggagacca tgtgcacccct catcacggcc atggatgcca atagtcagtt caccagcacc | 600 |
| tacatcctga ccgccatggc cattgaccgc tacctggcca ctgtccaccc catctcttcc | 660 |
| acgaagttcc ggaagccctc catggccacc ctggtgatct gcctcctgtg ggctctctcg | 720 |
| ttcattagca tcactcctgt gtggctctat gccaggctta tccccttccc aggggggtgct | 780 |
| gtgggctgtg catccgcct accaaacccca gatactgatc tttactggtt cactctgtat | 840 |
| cagtttttcc tggccttcgc ccttccgttt gtggtcatca ctgctgcgta cgtgaaaata | 900 |
| ctacagcgca tgacgtcttc ggtggcccca gcctctcaac gcagcatccg gcttcggaca | 960 |
| aagagggtga cccgcacagc cattgccatc tgtctggtct tctttgtgtg ctgggcgccc | 1020 |
| tactacgtgc tgcagctgac ccagttgtcc atcagccgcc cgaccctcac attcgtctac | 1080 |
| ctgtacaatg cggccatcag cttgggctat gccaacagct gcctcaatcc ctttgtgtac | 1140 |

```
atagtactct gtgagacctt tcgaaaacgc ttggtgctgt cggtgaagcc cgcggcccag    1200
gggcagcttc gcacggtcag caatgctcag acagctgacg aggagaggac agaaagcaaa    1260
ggcaccgtcg acgtaccgc gggcccggga tccatcgcca ccatggtgag caagggcgag    1320
gagctgttca ccggggtggt gcccatcctg gtcgagctgg acggcgacgt aaacggccac    1380
aagttcagcg tgtccggcga gggcgagggc gatgccacct acggcaagct gaccctgaag    1440
ttcatctgca ccaccggcaa gctgcccgtg ccctggccca ccctcgtgac cacccctgacc   1500 tacggcgtgc agtgcttcag ccgctacccc gaccacatga agcagcacga cttcttcaag    1560
tccgccatgc ccgaaggcta cgtccaggag cgcaccatct tcttcaagga cgacggcaac    1620
tacaagaccc gcgccgaggt gaagttcgag ggcgacaccc tggtgaaccg catcgagctg    1680
aagggcatcg acttcaagga ggacggcaac atcctggggc acaagctgga gtacaactac    1740
aacagccaca acgtctatat catggccgac aagcagaaga acggcatcaa ggtgaacttc    1800
aagatccgcc acaacatcga ggacggcagc gtgcagctcg ccgaccacta ccagcagaac    1860 accccatcg gcgacggccc cgtgctgctg cccgacaacc actacctgag cacccagtcc    1920
gccctgagca agacccccaa cgagaagcgc gatcacatgg tcctgctgga gttcgtgacc    1980
gccgccggga tcactctcgg catggacgag ctgtacaagt aa                      2022

<210> SEQ ID NO 30
<211> LENGTH: 35
<212> TYPE: DNA
<213> ORGANISM: Artificial Sequence
<220> FEATURE:
<223> OTHER INFORMATION: Linker

<400> SEQUENCE: 30
tcgacggtac cgcgggcccg ggatccatcg ccacc                               35

<210> SEQ ID NO 31
<211> LENGTH: 12
<212> TYPE: PRT
<213> ORGANISM: Artificial Sequence
<220> FEATURE:
<223> OTHER INFORMATION: Linker

<400> SEQUENCE: 31

Val Asp Gly Thr Ala Gly Pro Gly Ser Ile Ala Thr
 1               5                  10

<210> SEQ ID NO 32
<211> LENGTH: 29
<212> TYPE: DNA
<213> ORGANISM: Artificial Sequence
<220> FEATURE:
<223> OTHER INFORMATION: PCR primer

<400> SEQUENCE: 32
gcgaattcac catggatctg caagcctcg                                      29

<210> SEQ ID NO 33
<211> LENGTH: 28
<212> TYPE: DNA
<213> ORGANISM: Artificial Sequence
<220> FEATURE:
<223> OTHER INFORMATION: PCR primer

<400> SEQUENCE: 33
gcgtcgacgg tgcctttgct ttctgtcc                                       28
```

```
<210> SEQ ID NO 34
<211> LENGTH: 33
<212> TYPE: DNA
<213> ORGANISM: Artificial Sequence
<220> FEATURE:
<223> OTHER INFORMATION: PCR primer

<400> SEQUENCE: 34
ccttgctcac catggtgcct ttgctttctg tcc                           33

<210> SEQ ID NO 35
<211> LENGTH: 39
<212> TYPE: DNA
<213> ORGANISM: Artificial Sequence
<220> FEATURE:
<223> OTHER INFORMATION: PCR primer

<400> SEQUENCE: 35
cagaaagcaa aggcaccatg gtgagcaagg gcgaggagc                     39

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36
ggcggatcct ctagagtcgc ggcc                                     24

<210> SEQ ID NO 37
<211> LENGTH: 38
<212> TYPE: DNA
<213> ORGANISM: Artificial Sequence
<220> FEATURE:
<223> OTHER INFORMATION: PCR primer

<400> SEQUENCE: 37
gctctagagt cgcggccgct tacttgtaca gctcgtcc                      38
```

MELANIN CONCENTRATING HORMONE RECEPTOR CHIMERIC AND FUSION PROTEINS

CROSS-REFERENCE TO RELATED APPLICATIONS

The present application claims priority to provisional application U.S. Ser. No. 60/189,698, filed Mar. 15, 2000, hereby incorporated by reference herein.

BACKGROUND OF THE INVENTION

The references cited herein are not admitted to be prior art to the claimed invention.

Neuropeptides present in the hypothalamus play a major role in mediating the control of body weight. (Flier et al., 1998. *Cell,* 92, 437–440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon et al., 1990. *Mol. Endocrinol.* 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi et al., 1983. *Nature* 305, 321–323.)

In humans two genes encoding MCH have been identified that are expressed in the brain. (Breton et al., 1993. *Mol. Brain Res.* 18, 297–310.) In mammals MCH has been localized primarily to neuronal cell bodies of the hypothalamus which are implicated in the control of food intake, including perikarya of the lateral hypothalamus and zona inertia. (Knigge et al., 1996. *Peptides* 17, 1063–1073.)

Pharmacological and genetic evidence suggest that the primary mode of MCH action is to promote feeding (orexigenic). MCH mRNA is up regulated in fasted mice and rats and in the ob/ob mouse. (Qu et al., 1996. *Nature* 380, 243–247.) Injection of MCH centrally (ICV) stimulates food intake and MCH antagonizes the hypophagic effects seen with α-melanocyte stimulating hormone (αMSH). (Qu et al., 1996. *Nature* 380, 243–247.) MCH-deficient mice are lean, hypophagic, and have increased metabolic rate. (Shimada et al., 1998. *Nature* 396, 670–673.)

MCH action is not limited to modulation of food intake as effects on the hypothalamic-pituitary-axis have been reported. (Nahon 1994. *Critical Rev. in Neurobiol.* 8, 221–262.) MCH may be involved in the body response to stress as MCH can modulate the stress-induced release of CRP from the hypothalamus and ACTH from the pituitary. In addition, MCH neuronal systems may be involved in reproductive or maternal function.

Several references describe a receptor that is indicated to bind MCH. (Chambers et al., 1999. *Nature* 400, 261–265; Saito et al., 1999. *Nature* 400, 265–269; Bächner et al., 1999. *FEBS Letters* 457:522–524; Shimomura et al., 1999. *Biochemical and Biophysical Research Communications* 261, 622–626; and Lembo et al., 1999. *Nat. Cell Biol.* 1, 267–271.)

SUMMARY OF THE INVENTION

The present invention features melanin concentrating hormone receptor (MCH-R) chimeric and fusion proteins. MCH-R chimeric proteins comprise an MCH-R polypeptide region made up of at least two or more polypeptide regions characteristic of MCH-R found in different species. MCH-R fusion proteins comprise an MCH-R polypeptide region and a fluorescent protein region.

An MCH-R polypeptide region provides a functional G-protein coupled receptor region able to bind MCH and transduce an intracellular signal. Examples of MCH-R polypeptide regions include naturally occurring MCH-R, chimeric MCH-R containing two or more regions from naturally occurring MCH-R, and functional derivatives thereof.

Reference to the terms "characteristic" and "derivatives thereof" describe a relationship to a reference sequence. In both cases, there is at least about 75% sequence similarity to the reference sequence.

Thus, a first aspect of the present invention describes a fusion protein comprising (a) an MCH-R polypeptide region and (b) a fluorescent polypeptide region. The fluorescent polypeptide region is joined directly, or though a polypeptide linker, to the carboxy side of the MCH-R polypeptide region.

Another aspect of the present invention describes an MCH-R chimeric protein. The protein comprises: (a) an MCH-R binding region characteristic of a human MCH-R, (b) a transmembrane domain characteristic of a non-human MCH-R, and (c) an intracellular domain characteristic of a non-human MCH-R.

Another aspect of the present invention describes a nucleic acid encoding for an MCH-R fusion protein or an MCH-R chimeric protein described herein. Such nucleic acid comprises either a contiguous nucleotide sequence that codes for the protein or a sequence that is processed by a host cell to produce a contiguous nucleotide sequence encoding for the protein. Processing of a nucleic acid sequence to produce a contiguous nucleotide sequence encoding for a protein can occur by the splicing together of exons resulting in intron removal.

Another aspect of the present invention describes an expression vector comprising a nucleic acid encoding for an MCH-R fusion protein or an MCH-R chimeric protein described herein.

Another aspect of the present invention describes a recombinant cell comprising nucleic acid encoding for an MCH-R fusion protein or an MCH-R chimeric protein described herein. The nucleic acid may be part of the host genome or may exist independently of the host genome.

Another aspect of the present invention describes a non-human transgenic animal comprising nucleic acid encoding for an MCH-R fusion protein or an MCH-R chimeric protein described herein.

Another aspect of the present invention describes a method for assaying for MCH-R active compounds by measuring the effect of a test preparation on one or more MCH-R activities. The method is performed using either an MCH-R fusion protein or an MCH-R chimeric protein described herein.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1:
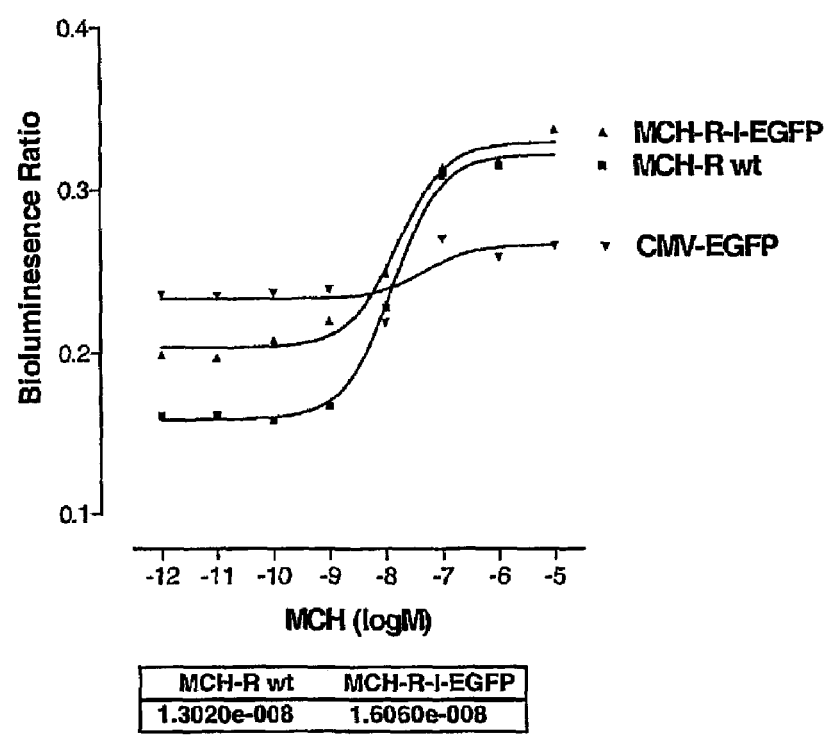
FIG. 1 illustrates aequorin assay results comparing a mouse MCH-R fusion with a human wild type MCH-R and a CMV-EGFP control.

The present invention features MCH-R chimeric and fusion proteins. Such proteins have a variety of different uses including being used as a research tool to study MCH-R function and dynamics, and being used to screen for MCH-R agonists and antagonists.

The MCH-R provides a target to achieve different beneficial effects in a patient. Preferably, MCH-R activity is modulated to achieve one or more of the following: weight loss, weight gain, treat cancer (e.g., colon or breast), reduce pain, treat diabetes, reduce stress, or teat sexual dysfunction.

Modulation of MCH-R activity can be achieved by evoking a response at the MCH receptor or by altering a response evoked by an MCH receptor agonist or antagonist. Compounds modulating MCH-R receptor activity include agonists, antagonists, and allosteric modulators. Generally, MCH-R antagonists and allosteric modulators negatively affecting activity will be used to achieve weight loss, treat cancer (e.g., colon or breast), reduce pain, reduce stress, or teat sexual dysfunction; and MCH-R agonists and allosteric modulators positively affecting activity will be used to produce a weight gain.

Preferably, MCH-R activity is modulated to achieve a weight loss or to treat diabetes in a patient. Diabetes mellitus can be treated by modulating MCH-R activity to achieve, for example, one or both of the following: enhancing glucose tolerance or decreasing insulin resistance.

Excessive body weight is a contributing factor to different diseases, including hypertension, diabetes, dyslipidemias, cardiovascular disease, gall stones, osteoarthritis, and certain forms of cancers. Bringing about a weight loss can be used, for example, to reduce the likelihood of such diseases and as part of a treatment for such diseases. Weight reduction can be achieved by modulating MCH-R activity to obtain, for example, one or more of the following effects: reducing appetite, increasing metabolic rate, reducing fat intake, or reducing carbohydrate craving.

Increasing body weight is particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy and radiation therapy.

MCH-R Chimeric Proteins

MCH-R chimeric proteins contain an MCH-R polypeptide region made up by at least two or more polypeptide regions characteristic of MCH-R found in different species. The different polypeptide regions that are present provide for an N-terminal extracellular domain; a transmembrane domain made up of transmembrane regions, extracellular loop regions, and intracellular loop regions; and an intracellular carboxy terminus domain. Examples of MCH-R amino acid sequences include the following: SEQ. ID. NO.1 (human MCH1R long form), SEQ. ID. NO. 2 (human MCH1R short form), and SEQ. ID. NO. 3 (mouse MCH1R).

Preferably, the MCH-R chimeric protein comprises an MCH-R binding region characteristic of a human MCH-R along with transmembrane and intracellular domains characteristic of a non-human MCH-R. There are substantial amino acid differences between the N-terminus of the MCH-R present in humans and that present in other species such as mice. Such differences could result in, for example, the mouse MCH-R having different intrinsic properties and responsiveness to agonists and/or antagonists than the human MCH-R. The presence of a human MCH-R binding region provides for a "humanized" MCH-R chimeric receptor.

The transmembrane and intracellular domains characteristic of a non-human MCH-R can be used in conjunction with a non-human host to provide a more naturally occurring environment for these regions. For example, an MCH-R chimeric having mouse transmembrane and intracellular domains are preferably used in murine cells lines or in transgenic mice.

MCH-R chimeric proteins may contain regions other than extracellular, transmembrane, and intracellular domains that do not substantially decrease the activity of the protein. Preferably, additional regions do not cause a decrease of more than about 25% of MCH-R activity as measured using one or more of the assays described in the examples provided below. Examples of additional regions that may be present include fluorescent protein regions and linker regions.

In an embodiment of the present invention, the MCH-R chimeric protein comprises: (a) an MCH binding region characteristic of a first species and (b) a transmembrane and intracellular domain region characteristic of a second species joined directly, or though a linker, to the carboxy side of the MCH binding region. Preferably, the protein comprises, consists, or consists essentially of an MCH-R polypeptide having a sequence similarity of at least about 75%, at least 85%, or at least 95% with either SEQ. D. NO. 4 (human short form/mouse species chimeric MCH1R) or SEQ. ID. NO. 5 (human long form/mouse species chimeric). Even more preferably, the protein comprises, consists essentially of, or consists of, SEQ. ID. NO. 4 or SEQ. ID. NO. 5.

Sequence similarity for polypeptides can be determined by BLAST. (Altschul et al., 1997. *Nucleic Acids Res.* 25, 3389–3402, hereby incorporated by reference herein.) In an embodiment of the present invention, sequence similarity is determined using tBLASTn search program with the following parameters: MATRIX:BLOSUM62, PER RESIDUE GAP COST:11, and Lambda ratio:1.

Differences in naturally occurring amino acids are due to different R groups. An R group effects different properties of the amino acid such as physical size, charge, and hydrophobicity. Amino acids can be divided into different groups as follows: neutral and hydrophobic (alanine, valine, leucine, isoleucine, proline, tryptophan, phenylalanine, and methionine); neutral and polar (glycine, serine, threonine, tyrosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acids groups can also be made. Preferably, such changes are made taking into account the position of the amino acid to be substituted in the polypeptide. For example, arginine can substitute more freely for nonpolor amino acids in the interior of a polypeptide then glutamate because of its long aliphatic side chain. (See, Ausubel, *Current Protocols in Molecular Biology*, John Wiley, 1987–1998, Supplement 33 Appendix 1C.)

MCH-R Fusion Proteins

MCH-R fusion proteins contain an MCH-R polypeptide region and a fluorescent protein region either directly joined together or joined together through a linker. These regions provide MCH-R activity and a marker for evaluating MCH-R dynamics.

An MCH-R polypeptide region provides functional MCH-R activity and includes naturally occurring MCH-R, chimeric MCH-R, and derivatives thereof. Preferred derivatives thereof have a sequence similarity of at least about 75%, at least about 85%, or at least about 95% to a naturally occurring MCH-R or a chimeric MCH-R described herein.

A fluorescent protein region contains a chromophore that fluoresces. Preferably, the fluorescent protein region is the green fluorescent protein of the jellyfish *Aequorea Victoria* or a derivative thereof. Preferred derivatives have a sequence similarity of at least about 75%, at least about 85%, or at least about 95% to the *Aequorea Victoria* green fluorescent protein (GFP). The *Aequorea Victoria* green fluorescent protein and examples of derivatives thereof are described by Cormack et al., 1996. *Gene* 17, 33–38; Yang et al., 1996. *Nucleic Acids Research* 24, 4592–4593; Tsien et al., U.S. Pat. No. 5,625,048; Tsien et al., U.S. Pat. No. 5,777,079; and Cormack et al., U.S. Pat. No. 5,804,387 (each of which are hereby incorporated by reference herein).

In different embodiments the MCH-R polypeptide region comprises, consists essentially of, or consists of, a sequence selected from the group consisting of: SEQ. ID. NO. 1, SEQ. ID. NO. 2, SEQ. ID. NO. 3, SEQ. ID. NO. 4, and SEQ. ID. NO. 5; and the fluorescent polypeptide region comprises, consists essentially of, or consists of, an amino acid sequence selected from the group consisting of SEQ. ID. NO. 6 (GFP), SEQ. ID. NO. 7 (EGFP), SEQ. ID. NO. 8 (Emerald), SEQ. ID. NO. 9 (Topaz), and SEQ. ID. NO. 10 (W1b). EGFP, Emerald, Topaz, and W1b are derivatives of GFP.

The optionally present linker is a polypeptide region that is preferably from 1 to about 100 amino acids in length. In different embodiments the linker is up to 75, 50 or 25 amino acids in length.

Preferably, the MCH-R fusion protein comprises, consists essentially of, or consists of, the MCH-R polypeptide region and the fluorescent polypeptide region. More preferably, the protein comprises, consists essentially of, or consists of, an amino acid sequence selected from the group consisting of: SEQ. ID. NO. 11 (mouse MCH1R-linker-EGFP), SEQ. ID. NO. 12 (mouse MCH1R/EGFP direct fusion), SEQ. ID. NO. 13 (human short form/mouse species chimeric MCH1R-linker-EGFP), or SEQ. ID. NO. 14 (human long form/mouse species chimeric MCH1R-linker-EGFP).

MCH-R Chimeric and Fusion Proteins Nucleic Acid and Expression

MCH-R chimeric and fusion proteins can be produced using techniques well known in the art. Preferably, such proteins are produced by recombinant expression inside a host cell by way of an expression vector or by way of nucleic acid integrated into the host genome. Examples of nucleic acid sequences encoding for MCH-R polypeptide regions, fluorescent protein regions, MCH-R chimeric proteins, and MCH-R fusion proteins are provided for by SEQ. ID. NOs. 15–29 (see Example 1, infra).

Starting with a particular amino acid sequence and the known degeneracy of the genetic code, a large number of different encoding nucleic acid sequences can be obtained. The degeneracy of the genetic code arises because almost all amino acids are encoded for by different combinations of nucleotide triplets or codons. The translation of a particular codon into a particular amino acid is well known in the art (see, e.g., Lewin *GENES IV*, p. 119, Oxford University Press, 1990). Amino acids are encoded for by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Examples of techniques for introducing nucleic acid into a cell and expressing the nucleic acid to produce protein are provided in references such as Ausubel, *Current Protocols in Molecular Biology*, John Wiley, 1987–1998, and Sambrook, et al., in *Molecular Cloning, A Laboratory Manual*, 2$^{nd}$ Edition, Cold Spring Harbor Laboratory Press, 1989.

An expression vector contains recombinant nucleic acid encoding for a polypeptide along with regulatory elements for proper transcription and processing. The recombinant nucleic acid contains two or more nucleic acid regions not naturally associated with each other. Exogenous regulatory elements such as an exogenous promoter can be useful for expressing recombinant nucleic acid in a particular host. Examples of expression vectors are cloning vectors, modified cloning vectors, specifically designed plasmids, and viruses.

Generally, the regulatory elements that are present in an expression vector include a transcriptional promoter, a ribosome binding site, a terminator, and an optionally present operator. Another preferred element is a polyadenylation signal providing for processing in eukaryotic cells. Preferably, an expression vector also contains an origin of replication for autonomous replication in a host cell, a selectable marker, a limited number of useful restriction enzyme sites, and a potential for high copy number.

Expression vectors providing suitable levels of polypeptide expression in different hosts are well known in the art. Mammalian expression vectors well known in the art include pcDNA3 (Invitrogen), pMC1neo (Stratagene), pXTI1 (Stratagene), pSG5 (Stratagene), EBO-pSV2-neo (ATCC 37593), pBPV-1(8–2) (ATCC 37110), pdBPV-MMTneo(342–12) (ATCC 37224), pRSVgpt (ATCC 37199), pRSVneo (ATCC 37198), pSV2-dhfr (ATCC 37146), pUCTag (ATCC 37460), pCI-neo (Promega) and .lambda.ZD35 (ATCC 37565). Bacterial expression vectors well known in the art include pET11a (Novagen), lambda gt11 (Invitrogen), pcDNAII (Invitrogen), and pKK223-3 (Pharmacia). Fungal cell expression vectors well known in the art include pYES2 (Invitrogen) and Pichia expression vector (Invitrogen). Insect cell expression vectors well known in the art include Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey, hampster, and rodent; and insect cells such as Drosophila and silkworm derived cell lines. Commercially available mammalian cell lines include L cells L-M(TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

To enhance expression in a particular host it may be useful to modify the sequence to take into account codon usage of the host. Codon usage of different organisms are well known in the art. (See, Ausubel, *Current Protocols in Molecular Biology*, John Wiley, 1987–1998, Supplement 33 Appendix 1C.)

Expression vectors may be introduced into host cells using standard techniques. Examples of such techniques include transformation, transfection, lipofection, protoplast fusion, and electroporation.

Nucleic acid encoding for a polypeptide can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Techniques for producing transgenic animals are well known in the art. Examples of such techniques are provided for by Teratocarcinomas and embryonic stem cells: a practical approach. Ed. By E. J. Robertson, IRL Press Limited, Oxford, England (1987); and Gene Targeting: a practical approach. Ed. By A. L. Joyner, Oxford University Press Inc. New York, N.Y. (1993).

G-Protein Coupled Receptor Assays

MCH-R is G-protein coupled receptor. Techniques for measuring different G-protein activities, such as Gi/o, Gs, and Gq are well known in the art. MCH-R activity is preferably assayed for by measuring either Gi/o or Gq.

Gi/o and Gs activity can be measured using techniques such as a melonaphore assay, measuring cAMP production, measuring inhibition of cAMP accumulation, and measuring binding of $^{35}$S-GTP. cAMP can be measured using different techniques such as radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button et al., 1993. *Cell Calcium* 14, 663–671, and Feighner et al., 1999. *Science* 284, 2184–2188, both of which are hereby incorporated by reference herein.)

Functional assays can be performed using individual compounds or preparations containing different compounds. A preparation containing different compounds where one or more compounds affect MCH-R chimeric or fusion protein activity can be divided into smaller groups of compounds to identify the compound(s) affecting MCH-R chimeric or fusion protein activity. In an embodiment of the present invention a test preparation containing at least 10 compounds is used in a functional assay.

Functional assays can be performed using recombinantly produced MCH-R chimeric or fusion protein present in different environments. Such environments include, for example, cell extracts and purified cell extracts containing the MCH-R chimeric or fusion protein expressed from recombinant nucleic acid and an appropriate membrane for the polypeptide; and the use of a purified MCH-R chimeric or fusion protein produced by recombinant means that is introduced into a different environment suitable for measuring G-protein activity.

Fluorescent Protein Assays

Fluorescent protein joined to an MCH receptor can be employed to study different aspects of receptor dynamics including receptor sequestration, receptor densitization, and receptor localization. The fluorescent protein can be used in in vitro or in vivo systems.

In vitro applications of fluorescent proteins can be performed using techniques well known in the art. Examples of such techniques are provided by Barak et al., 1997. *Mol Pharm.* 5, 177–184; Tarasova et al., 1997. *J. Biol. Chem.* 272, 14817–14824; Lin et al., 1998. *Mol. Cell. Endo.* 146, 27–37; Tarasova et al., 1998. *J. Biol. Chem.* 273, 15883–15886; Kallal et al., 1998. *J. Biol. Chem.* 273, 322–328; Groake et al., 1999. *J. Biol. Chem.* 274, 23263–23269; Doherty et al., 1999. *Biochem. J.* 341, 415–422; crock et al. 10128; Cornea et al., 1999. *Endocrinology* 140, 4272–4280; and Lembo et al., 1999. *Nat. Cell Biol.* 1, 267–271 (these references are not admitted to be prior art to the claimed invention).

In vivo applications of fluorescent proteins can be performed using techniques well known in the art. Examples of such techniques are provided by Mombaerts et al., 1996. *Cell* 87, 675–686; Rodriquez et al., 1999. *Cell* 97, 199–208;

Spergel et al., 1999. *J. Neurosci.* 1, 2037–2050; and Zuo et al., 1999. *Proc. Natl. Acad. Sci. USA* 96, 14100–14105 (these references are not admitted to be prior art to the claimed invention).

EXAMPLES

Examples are provided below to further illustrate different features and advantages of the present invention. The examples also illustrate useful methodology for practicing the invention. These examples do not limit the claimed invention.

Example 1

Amino acid and nucleic acid sequence information for SEQ. ID. NOs. 1–29 are provided below. SEQ. ID. NOs. 1–29 include examples of polypeptide and encoding nucleic acid sequences for MCH-R polypeptide regions, fluorescent polypeptide regions, fusion proteins and chimeric proteins. In some cases the encoding nucleic acid is shown with additional nucleic acid upstream or downstream from an open reading frame.

```
Human long form MCH1R:
MSVGAMKKGVGRAVGLGGGSGCQATEEDPLPNCGACA   SEQ. ID. NO.1

PGQGGRRWRLPQPAWVEGSSARLWEQATGTGWMDLEA

SLLPTGPNASNTSDGPDNLTSAGSPPRTGSISYTIIM

PSVFGTICLLGIIGNSTVIFAVVKKSKLHWCNNVPDI

FIINLSVVDLLFLLGMPFMIHQLMGNGVWHFGETMCT

LITAMDANSQFTSTYILTAMAIDRYLATVHPISSTKF

RKPSVATLVICLLWALSFISITPVWLYARLIPFPGGA

VGCGIRLPNPDTDLYWFTLYQFFLAFALPFVVITAAY

VRILQRMTSSVAPASQRSIRLRTKRVTRTAIAICLVF

FVCWAPYYVLQLTQLSISRPTLTFVYLYNAAISLGYA

NSCLNPFVYIVLCETFRKRLVLSVKPAAQGQLRAVSN

AQTADEERTESKGT

Human short form MCH1R:
MDLEASLLPTGPNASNTSDGPDNLTSAGSPPRTGSIS   SEQ. ID. NO.2

YINIIMPSVFGTICLLGIIGNSTVIFAVVKKSKLHWC

NNVPDIFIINLSVVDLLFLLGMPFMIHQLMGNGVWHF

GETMCTLITAMDANSQFTSTYILTAMAIDRYLATVHP

ISSTKFRKPSVATLVICLLWALSFISITPVWLYARLI

PFPGGAVGCGIRLPNPDTDLYWFTLYQFFLAFALPFV

VITAAYVRILQRMTSSVAPASQRSIRLRTKRVTRTAI

AICLVFFVCWAPYYVLQLTQLSISRPTLTFVYLYNAA

ISLGYANSCLNPFVYIVLCETFRKRLVLSVKPAAQGQ

LRAVSNAQTADEERTESKGT

Mouse MCH1R:
MDLQASLLSTGPNASNISDGQDNFTLAGPPPRTRSVS   SEQ. ID. NO.3

YINIIMPSVFGTICLLGIVGNSTVIFAVVKKSKLHWC

SNVPDIFIINLSVVDLLFLLGMPFMIHQLMGNGVWHF

GETMCTLITAMDANSQFTSTYILTAMAIDRYLATVHP

ISSTKFRKPSMATLVICLLWALSFISITPVWLYARLI

PFPGGAVGCGIRLPNPDTDLYWFTLYQFFLAFALPFV

VITAAYVKILQRMTSSVAPASQRSIRLRTKRVTRTAI

AICLVFFVCWAPYYVLQLTQLSISRPTLTFVYLYNAA

ISLGYANSCLNPFVYIVLCETFRKRLVLSVKPAAQGQ

LRTVSNAQTADEERTESKGT

Human short form/mouse species chimeric MCH1R:
MDLEASLLPTGPNASNTSDGPDNLTSAGSPPRTGSIS   SEQ. ID. NO.4

YINIIMIPSVFGTICLLGIIGNSTVIFAVVKKSKLHW

CNNVPDIFIINLSVVDLLFLLGMPFMIHQLMGNGVWH

FGETMCTLITAMDANSQFTSTYILTAMAIDRYLATVH

PISSTKFRKPSMATLVICLLWALSFISITPVWLYARL

IPFPGGAVGCGIRLPNPDTDLYWFTLYQFFLAFALPF

VVITAAYVKILQRMTSSVAPASQRSIRLRTKRVTRTA

IAICLVFFVCWAPYYVLQLTQLSISRPTLTFVYLYNA

AISLGYANSCLNPFVYIVLCETFRKRLVLSVKPAAQG

QLRTVSNAQTADEERTESKGT

Human long form/mouse species chimeric MCH1R:
MSVGAMKKGVGRAVGLGGGSGCQATEEDPLPNCGACA   SEQ. ID. NO.5

PGQGGRRWRLPQPAWVEGSSARLWEQATGTGWMDLEA

SLLPTGPNASNTSDGPDNLTSAGSPPRTGSISYIIIM

PSVFGTICLLGIIGNSTVIFAVVKKSKLHWCNNVPDI

FIINLSVVDLLFLLGMPFMIHQLMGNGGVWHFGETMC

TLITAMDANSQFTSTYILTAMAIDRYLATVHPISSTK

FRKPSMATLVICLLWALSFISITPVWLYARLIPFPGG

AVGCGIRLPNPDTDLYWFTLYQFFLAFALPFVVITAA

YVKILQRMTSSVAPASQRSIRLRTKRVTRTAIAICLV

FFVCWAPYYVLQLTQLSISRPTLTFVYLYNAAISLGY

ANSCLNPFVYIVLCETFRKRLVLSVKPAAQGQLRTVS

NAQTADEERTESKGT

GEP:
MSKGEELFTGVVPILVELDGDVNGHKFSVSGEGEGDA   SEQ. ID. NO.6

TYGKLTLKFICTTGKLPVPWPTLVTTFSYGVQCFSRY

PDHMKQHDFFKSAMPEGYVQERTIFFKDDGNYKTRAE

VKFEGDTLVNRIELKGIDFKEDGNILGHKLEYNYNSH

NVYIMADKQKNGIKVNFKIRHNIEDGSVQLADHYQQN

TPIGDGPVLLPDNHYLSTQSALSKDPNEKRDHMVLLE

PVTAAGITHGMDELYK

EGEP:
MVSKGEELFTGVVPILVELDGDVNGHKFSVSGEGEGD   SEQ. ID. NO.7
```

-continued
ATYGKLTLKFICTTGKLPVPWPTLVTTLTYGVQCFSR

YPDHMKQHDFFKSAMPEGYVQERTIFFKDDGNYKTRA

EVKFEGDTLVNRIELKGIDFKEDGNILGHKLEYNYNS

HNVYIMADKQKNGILKVNFKIRHNIEDGSVQLADHYQ

QNTPIGDGPVLLPDNHYLSTQSALSKDPNEKRDHMVL

LEFVTAAGITLGMDELYK

SEQ. ID. NO. 8: Emerald
Met Val Ser Lys Gly Glu Glu Leu Phe Thr Gly Val Val Pro Ile Leu Val Glu Leu Asp Gly Asp Val Asn Gly His Lys Phe Ser Val Ser Gly Glu Gly Glu Gly Asp Ala Thr Tyr Gly Lys Leu Thr Leu Lys Phe Ile Cys Thr Thr Gly Lys Leu Pro Val Pro Trp Pro Thr Leu Val Thr Thr Leu Thr Tyr Gly Val Gln Cys Phe Ala Arg Tyr Pro Asp His Met Lys Gln His Asp Phe Phe Lys Ser Ala Met Pro Glu Gly Tyr Val Gln Glu Arg Thr Ile Phe Phe Lys Asp Asp Gly Asn Tyr Lys Thr Arg Ala Glu Val Lys Phe Glu Gly Asp Thr Leu Val Asn Arg Ile Glu Leu Lys Gly Ile Asp Phe Lys Glu Asp Gly Asn Ile Leu Gly His Lys Leu Glu Tyr Asn Tyr Asn Ser His Lys Val Tyr Ile Thr Ala Asp Lys Gln Lys Asn Gly Ile Lys Val Asn Phe Lys Thr Arg His Asn Ile Glu Asp Gly Ser Val Gln Leu Ala Asp His Tyr Gln Gln Asn Thr Pro Ile Gly Asp Gly Pro Val Leu Leu Pro Asp Asn His Tyr Leu Ser Thr Gln Ser Ala Leu Ser Lys Asp Pro Asn Glu Lys Arg Asp His Met Val Leu Leu Glu Phe Val Thr Ala Ala Gly Ile Thr Leu Gly Met Asp Glu Leu Tyr Lys SEQ. ID. NO. 9: Topaz
Met Val Ser Lys Gly Glu Glu Leu Phe Thr Gly Val Val Pro Ile Leu Val Glu Leu Asp Gly Asp Val Asn Gly His Lys Phe Ser Val Ser Gly Glu Gly Glu Gly Asp Ala Thr Tyr Gly Lys Leu Thr Leu Lys Phe He Cys Thr Thr Gly Lys Leu Pro Val Pro Trp Pro Thr Leu Val Thr Thr Phe Gly Tyr Gly Val Gln Cys Phe Ala Arg Tyr Pro Asp His Met Arg Gln His Asp Phe Phe Lys Ser Ala Met Pro Glu Gly Tyr Val Gln Glu Arg Thr Ile Phe Phe Lys Asp Asp Gly Asn Tyr Lys Thr Arg Ala Glu Val Lys Phe Glu Gly Asp Thr Leu Val Asn Arg Ile Glu Leu Lys Gly Ile Asp Phe Lys Glu Asp Gly Asn Ile Leu Gly His Lys Leu Glu Tyr Asn Tyr Asn Ser His Asn Val Tyr Ile Met Ala Asp Lys Gln Lys Asn Gly Ile Lys Val Asn Phe Lys Ile Arg His Asn Ile Glu Asp Gly Ser Val Gln Leu Ala Asp His Tyr Gln Gln Asn Thr Pro Ile Gly Asp Gly Pro Val Leu Leu Pro Asp Asn His Tyr Leu Ser Tyr Gln Ser Ala Leu Ser Lys Asp Pro Asn Glu Lys Arg Asp His Met Val Leu Leu Glu Phe Val Thr Ala Ala Gly Ile Thr Leu Gly Met Asp Glu Leu Tyr Lys SEQ. ID. NO. 10: W1B
Met Val Ser Lys Gly Glu Glu Leu Phe Thr Gly Val Val Pro Ile Leu Val Glu Leu Asp Gly Asp Val Asn Gly His Arg Phe Ser Val Ser Gly Glu Gly Glu Gly Asp Ala Thr Tyr Gly Lys Leu Thr Leu Lys Phe Ile Cys Thr Thr Gly Lys Leu Pro Val Pro Trp Pro Thr Leu Val Thr Thr Leu Thr Trp Gly Val Gln Cys Phe Ser Arg Tyr Pro Asp His Met Lys Gln His Asp Phe Phe Lys Ser Ala Met Pro Glu Gly Tyr Val Gln Glu Arg Thr Ile Phe Phe Lys Asp Asp Gly Asn Tyr Lys Thr Arg Ala Glu Val Lys Phe Glu Gly Asp Thr Leu Val Asn Arg Ile Glu Leu Lys Gly Ile Asp Phe Lys Glu Asp Gly Asn Ile Leu Gly His Lys Leu Glu Tyr Asn Tyr Ile Ser His Asn Val Tyr Ile Thr Ala Asp Lys Gln Lys Asn Gly Ile Lys Val Ala His Phe Lys Ile Arg His Asn Ile Glu Asp Gly Ser Val Gln Leu Ala Asp His Tyr Gln Gln Asn Thr Pro Ile Gly Asp Gly Pro Val Leu Leu Pro Asp Asn His Tyr Leu Ser Thr Gln Ser Ala Leu Ser Lys Asp Pro Asn Glu Lys Arg Asp His Met Val Leu Leu Glu Phe Val Thr Ala Ala Gly Ile Thr Leu Gly Met Asp Glu Leu Tyr Lys Mouse MCH1R-linker-EGFP:
SEQ. ID. NO.11
MDLQASLLSTGPNASNISDGQDNFTLAGPPPRTRSVSYINIIMPSVFGTI

CLLGIVGNSTVIFAVVKKSKLHWCSNVPDIFIINLSVVDLLFLLGMPFMI

HQLMGNGVWHFGETMCTLITAMDANSQFTSTYILTAMAIDRYLATVHPIS

STKFRKPSMATLVICLLWALSFISITPVWLYARLIPFPGGAVGCGIRLPN

PDTDLYWFTLYQFFLAFALPFVVITAAYVKILQRMTSSVAPASQRSIRLR

TKRVTRTAIAICLVFFVCWAPYYVLQLTQLSISRPTLTFVYLYNAAISLG

YANSCLNPFVYIVLCETFRKRLVLSVKPAAQGQLRTVSNAQTADEERTES

KGTVDGTAGPGSIATMVSKGEELFTGVVPILVELDGDVNGHKFSVSGEGE

GDATYGKLTKFICTTGKLPVPWPTLVTTLTYGVQCFSRYPDHMKQHDFFK

SAMPEGYVQERTIFFKDDGNYKTRAEVKFEGDTLVNRIELKGIDFKEDGN

ILGHKLEYNYNSHNVYIMADKQKNGIKVNFKIRHNIEDGSVQLADHYQQN

TPIGDGPVLLPDNHYLSTQSALSKDPNEKRDHMVLLEFVTAAGITLGMDE

LYK

Mouse MCH1R/EGFP direct fusion:
SEQ. ID. NO.11
MDLQASLLSTGPNASNISDGQDNFTLAGPPPRTRSVSYINIIMPSVFGTI

CLLGIVGNSTVIFAVVKKSKLHWCSNVPDIFLIINLSVVDLLFLLGMPFM

IHQLMGNGVWHFGETMCTLITAMDANSQFTSTYILTAMAIDRYLATVHPI

SSTKFRKPSMATLVICLLWALSFISITPVWLYARLIPPGGAVGCGIRLPN

PDTDLYWFTLYQFFLAFALPFVVITAAYVKILQRMTSSVAPASQRSIRLR

TKRVTRTAIAICLVFFVCWAPYYVLQLTQLSISRPTLTFVYLYNAAISLG

YANSCLNPFVYIVLCETFRKRLVLSVKPAAQGQLRTVSNAQTADEERTES

KGTMVSKGEELFTGVVPILVELDGDVNGHKFSVSGEGEGDATYGKLTLKF

ICTTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYNYN

SHNVYLMADKQKNGIKVNFKIRHNIEDGSVQLADHYQQNTPIGDGPVLLP

DNHYLSTQSALSKDPNEKRDHMVLLEFVTAAGITLGMDELYK

Human short form/mouse species chimeric MCH1R-linker-EGEP:
SEQ. ID. NO.13
MDLEASLLPTGPNASNTSDGPDNLTSAGSPPRTGSISYINIIMPSVFGTI

CLLGIIGNSTVIFAVVKKSKLHWCNNVPDIFIINLSVVDLLFLLGMPFMI

HQLMGNGVWHFGETMCTLITAMDANSQFTSTYILTAMAIDRYLATVIHPI

SSTKFRKPSMATLVICLLWALSFISTPVWLYARLIPFPGGAVGCGIRLPN

PDTDLYWFTLYQFFLAFALPFVVITAAYVKILQRMTSSVAPASQRSIRLR

TKRVTRTAIAICLVFFVCWAPYYVLQLTQLSISRPTLTFVYLYNAAISLG

YANSCLNPFVYIVLCETFRKRLVLSVKPAAQGQLRTVSNAQTADEERTES

KGTVDGTAGPGSIATMVSKGEELFTGVVPILVELDGDVNGHKFSVSGEGE

GDATYGKLTLKFICTTGKLPVPWPTLVTLLTYGVQCFSRYPDHMKQHDFF

KSAMPEGYVQERTIFFKDDGNYKTRAEVKFEGDTLVNRIELKGIDFKEDG

-continued
NILGHKLEYNYNSHNVYIMADKQKNGIKVNFKIRHNIEDGSVQLADHYQQ

NTPIGDGPVLLPDNHYLSTQSALSKDPNEKRDHMVLLEFVTAAGITLGMD

ELYK

Human long form/mouse species chimeric
MCHLR-linker-EGFP:
SEQ. ID. NO.14
MSVGAMKKGVGRAVGLGGGSGCQATEEDPLPNCGACAPGQGGRRWRLPQP

AWVEGSSARLWEQATGTGWMDLEASLLPTGPNASNTSDGPDNLTSAGSPP

RTGSISYINIIMPSVFGTICLLGIIGNSTVIFAVVKKSKLHWCNNVPDIF

IINLSVVDLLFLLGMPFMIHQLMGNGVWHFGETMCTLITAMDANSQFTST

YILTAMAIDRYLATVHPISSTKFRKPSMATLVICLLWALSFISITPVWLY

ARLIPFPGGAVGCGIRLPNPDTDLYWFTLYQFFLAFALPFVVITAAYVKI

LQRMTSSVAPASQRSIRLRTKRVTRTAIAICLVFFVCWAPYYVLQLTQLS

ISRPTLTFVYLYNAAISLGYANSCLNPFVYIVLCETFRKRLVLSVKPAAQ

GQLRTVSNAQTADEERTESKGTVDGTAGPGSIATMVSKGEELFTGVVPIL

VELDGDVNGHKFSVSGEGEGDATYGKLTLKFICTTGKLPVPWPTLVTTLT

YGVQCFSRYPDHMKQHDFFKSAMPEGYVQERTIFFKDDGNYKTRAEVKFE

GDTLVNRIELKGIDFKEDGNILGHKLEYNYNSHNVYIMADKQKNGIKVNF

KIRHNIEDGSVQLADHYQQNTPIGDGPVLLPDNHYLSTQSALSKDPNEKR

DHMVLLEFVTAAGITTGMDELYK

Human long form MCH1R cDNA:
SEQ. ID. NO.15
ATGTCAGTGGGAGCCATGAAGAAGGGAGTGGGGAGGGCAGTTGGGCTTGG

AGGCGGCAGCGGCTGCCAGGCTACGGAGGAAGACCCCCTTCCCAACTGCG

GGGCTTGCGCTCCGGGACAAGGTGGCAGGCGCTGGAGGCTGCCGCAGCCT

GCGTGGGTGGAGGGGAGCTCAGCTCGGTTGTGGGAGCAGGCGACCGGCAC

TGGCTGGATGGACCTGGAAGCCTCGCTGCTGCCCACTGGTCCCAACGCCA

GCAACACCTCTGATGGCCCCGATAACCTCACTTCGGCAGGATCACCTCCT

CGCACGGGGAGCATCTCCTACATCAACATCATCATGCCTTCGGTGTTCGG

CACCATCTGCCTCCTGGGCATCATCGGGAACTCCACGGTCATCTTCGCGG

TCGTGAAGAAGTCCAAGCTGCACTGGTGCAACAACGTCCCCGACATCTTC

ATCATCAACCTCTCGGTAGTAGATCTCCTCTTTCTCCTGGGCATGCCCTT

CATGATCCACCAGCTCATGGGCAATGGGGTGTGGCACTTTGGGGAGACCA

TGTGCACCCTCATCACGGCCATGGATGCCAATAGTCAGTTCACCAGCACC

TACATCCTGACCGCCATGGCCATTGACCGCTACCTGGCCACTGTCCACCC

CATCTCTTCCACGAAGTTCCGGAAGCCCTCTGTGGCCACCCTGGTGATCT

GCCTCCTGTGGGCCCTCTCCTTCATCAGCATCACCCCTGTGTGGCTGTAT

GCCAGACTCATCCCCTTCCCAGGAGGTGCAGTGGGCTGCGGCATACGCCT

GCCCAACCCAGACACTGACCTCTACTGGTTCACCCTGTACCAGTTTTTCC

TGGCCTTTGCCCTGCCTTTTGTGGTCATCACAGCCGCATACGTGAGGATC

CTGCAGCGCATGACGTCCTCAGTGGCCCCCGCCTCCCAGCGCAGCATCCG

GCTGCGGACAAAGAGGGTGACCCGCACAGCCATCGCCATCTGTCTGGTCT

TCTTTGTGTGCTGGGCACCCTACTATGTGCTACAGCTGACCCAGTTGTCC

ATCAGCCGCCCGACCCTCACCTTTGTCTACTTATACAATGCGGCCATCAG

CTTGGGCTATGCCAACAGCTGCCTCAACCCCTTTGTGTACATCGTGCTCT

GTGAGACGTTCCGCAAACGCTTGGTCCTGTCGGTGAAGCCTGCAGCCCAG

GGGCAGCTTCGCGCTGTCAGCAACGCTCAGACGGCTGACGAGGAGAGGAC

AGAAAGCAAAGGCACCTGA

Human short form MCHLR cDNA:
SEQ. ID. NO.16
ATGGACCTGGAAGCCTCGCTGCTGCCCACTGGTCCCAATGCCAGCAACAC

CTCTGATGGCCCCGATAACCTCACTTCGGCAGGATCACCTCCTCGCACGG

GGAGCATCTCCTACATCAACATCATCATGCCTTCGGTGTTCGGCACCATC

TGCCTCCTGGGCATCATCGGGAACTCCACGGTCATCTTCGCGGTCGTGAA

GAAGTCCAAGCTGCACTGGTGCAACAACGTCCCCGACATCTTCATCATCA

ACCTCTCGGTAGTAGATCTCCTCTTTCTCCTGGGCATGCCCTTCATGATC

CACCAGCTCATGGGCAATGGGGTGTGGCACTTTGGGGAGACCATGTGCAC

CCTCATCACGGCCATGGATGCCAATAGTCAGTTCACCAGCACCTACATCC

TGACCGCCATGGCCATTGACCGCTACCTGGCCACTGTCCACCCCATCTCT

TCCACGAAGTTCCGGAAGCCCTCTGTGGCCACCCTGGTGATCTGCCTCCT

GTGGGCCCTCTCCTTCATCAGCATCACCCCTGTGTGGCTGTATGCCAGAC

TCATCCCCTTCCCAGGAGGTGCAGTGGGCTGCGGCATACGCCTGCCCAAC

CCAGACACTGACCTCTACTGGTTCACCCTGTACCAGTTTTTCCTGGCCTT

TGCCCTGCCTTTTGTGGTCATCACAGCCGCATACGTGAGGATCCTGCAG

CGCATGACGTCCTCAGTGGCCCCCGCCTCCCAGCGCAGCATCCGGCTGCG

GACAAAGAGGGTGACCCGCACAGCCATCGCCATCTGTCTGGTCTTCTTTG

TGTGCTGGGCACCCTACTATGTGCTACAGCTGACCCAGTTGTCCATCAGC

CGCCCGACCCTCACCTTTGTCTACTTATACAATGCGGCCATCAGCTTGGG

CTATGCCAACAGCTGCCTCAACCCCTTTGTGTACATCGTGCTCTGTGAGA

CGTTCCGCAAACGCTTGGTCCTGTCGGTGAAGCCTGCAGCCCAGGGGCAG

CTTCGCGCTGTCAGCAACGCTCAGACGGCTGACGAGGAGGACAGAAAG

CAAAGGCACCTGA

Mouse MCH1R cDNA: Nucleic acid sequence start and
stop codons are highlighted:
SEQ. ID. NO.17
GGCGGTAGAGGAAGACCCTTTTCTGGACTGCGGGGCTCAAGCTCCGGACA

AGGCGGTGGAGGGCGCTGQAGGCTGCCGCAGCCTGCGTGGGTGGACGGGC

GCTCCACTCCAGGGAGCAGGCGACCTGCACCGGCTGCATGGATCTGCAAG

CCTCGTTGCTGTCCACTGGCCCCAATGCCAGCAACATCTCCGATGGCCAG

GATAATTTCACATTGGCGGGGCCACCTCCTCGCACAAGGAGTGTCTCCTA

CATCAACATCATCATGCCTTCAGTGTTTGGTACCATCTGTCTCCTGGGCA

TTGTGGGAAACTCCACAGTCATTTTTGCCGTGGTGAAGAAATCCAAGCTG

CACTGGTGCAGCAACGTCCCTGACATCTTCATCATCAACCTCTCTGTGGT

GGATCTGCTTTTCCTGCTGGGCATGCCTTTCATGATCCACCAGCTCATGG

GTAATGGTGTCTGGCACTTTGGGGAAACCATGTGCACCCTCATCACAGCC

```
ATGGACGCCAACAGTCAGTTCACCAGCACCTACATCCTGACTGCTATGGC
CATTGACCGCTACTTGGCCACCGTCCATCCCATCTCCTCCACCAAGTTCC
GGAAGCCCTCCATGGCCACCCTGGTGATCTGCCTCCTGTGGGCTCTCTCG
TTCATTAGCATCACTCCTGTGTGGCTCTATGCCAGGCTTATCCCCTTCCC
AGGGGGTGCTGTGGGCTGTGGCATCCGCCTACCAAACCCAGATACTGATC
TTTACTGGTTCACTCTGTATCAGTTTTTCCTGGCCTTCGCCCTTCCGTTT
GTGGTCATCACTGCTGCGTACGTGAAAATACTACAGCGCATGACGTCTTC
GGTGGCCCCAGCCTCTCAACGCAGCATCCGGCTTCGGACAAAGAGGGTGA
CCCGCACAGCCATTGCCATCTGTCTGGTCTTCTTTGTGTGCTGGGCGCCC
TACTACGTGCTGCAGCTGACCCAGTTGTCCATCAGCCGCCCGACCCTCAC
ATTCGTCTACCTGTACAATGCGGCCATCAGCTTGGGCTATGCCAACAGCT
GCCTCAATCCCTTTGTGTACATAGTACTCTGTGAGACCTTTCGAAAACGC
TTGGTGCTGTCGGTGAAGCCCGCGGCCCAGGGGCAGCTTCGCACGGTCAG
CAATGCTCAGACAGCTGACGAGGAGGAGGACAGAAAGCAAAGGCACCTGAC
AATCCCCCCGGTCACCTCCAAGTCAGGTCACCGCATCAAACCATGGGGA
GAGATACTGAGATAAACCCGGGGCTACCCTGGGAGGATGCAGAAGCTGGA
GGCTGGGGGCTTGTAGCAAACCACATTCCACGGGGCCCACAAATTGCTAG
GGAGGCTTGCAGCCTGGTTTGGGGGGAAGCCTCAGACTGCAGGGATCCC
CTTGACAGAATAGAAGCGGAGCAAGAAGGAAAGGGTGGTTTGACTGGTTC
TCGGGGTCTGTATCTGTTGGCTCGCATATATCTTTCTCTCAAGGGAAGAA
GGCGGAGGTGCCTAGCTGGGTTCCTTTAAAACTAGGCAGGGCTAGGATCT
GAGCAGCTAGGGCTCTACTGTGAGACTGGGCAAGCCGAGCGTTCCCTCCC
ATCTCTCATTGGTGTTGATAGAAGGCAGTCTTTCTCCCAAGCTGGTGGAT
CTCCTGAAGCACGCTGCCTGGGCTCCAGCATCCTGTGCGGATTTCACGTT
CTCTTTAGGGGATGCATGTTGACACTGGGGTGTGGGCTCTGAGCCCACAG
GAGTTTAAAAAACCAAAAGAGCTCAGAGTGTCGAGAGAGACCCAATCACC
GAGAATGACAAGGCAACCTGGGGTGGATGGATCTTGAAACTAATAAAA
AGGGGTTTTCACAGTGACAGCGACATTCTCTTCATAGGGCACAGCTGTCA
GTCTATGGCTGATCCAGAGCGAGCATCCATGAATTCTGCATGTGCAGGGG
TCACTCTAATACCTGATATGTTGGCATCATCTTTGTGCTTGAGCCTTCCN
CTCCCAAATGGGAATGAAATAAAGGCAAATTCCCNCCCCCCCCAAAAAAG
GGGNAAAAAAAAAAAAAAAAAAAAAAAAAAA
```
Mouse MCH1R genomic DNA: Nucleic acid sequence start and stop codons, as well as intron borders, are highlighted:
SEQ. ID. NO.18
```
GGCGGTAGAGGAAGACCCTTTTCTGGACTGCGGGGCTCAAGCTCCGGACA
AGGCGGTGGAGGGCGCTGGAGGCTGCCGCAGCCTGCGTGGTGGACGGGC
GCTCCACTCCAGGGAGCAGGCGACCTGCACCGGCTGCATGGATCTGCAAG
CCTCGTTGCTGTCCACTGGCCCCAATGCCAGCAACATCTCCGATGGCCAG
GATAATTTCACATTGGCGGGTGAGTCGAGTTGGAGTCCTCCCTCCTCCGG
GATGGGTGTGGAAAATGGGAAGGTTTCACCTCCCAAGCCAAACTGCCTGG
GAAACTTTATCTTACAGTTCTTGGTGATAAGATCTGCAGTCGGCTTTGCC
TGAAGAGGAAGAGGAGAGGAGGGGACACCAGCTAGGACAGAAGGGGCAGG
GAGGAATAGAGATGGGGCAGAGGCACATTTAGAAACAACAAGGGTTGGTG
ACAAGACGTGAGGCAGGCAGGCTTGAGGGGAAAGCTTGCTGATGAGTCCC
AAATATGCTTTGCAGGGGGGGGGGGGGGAATCAAGGCTGGAGAAGCAA
GCAAGCAAGACAGCAAGACAGCGGGCGGGTAGTATGTGGGAGCCAGCAGA
AGCGCTTTGATTCACCGCTATCCTGGGCTCAATCCTCTGGCCTCGCACTG
GGGAAATGGGGTCTGAGTGGTCCTTGCTGTCTTCTGGCAAAGGCTGCTGG
GAGCAAAAGACTTCACAGGGCGTGAGAGGATTAACTTTTCTGGTGAATTA
AGCTTCTTGACATTTGCAGAACGTCAATGCCTTAAAATTCTAGCTCTGAA
GGAGAAGGGAATGAAGGGGAAAGAGGGAAGGTTGGTGTGGAGAAATTCCC
AAGCTTCTGGGGTGTAACACAGCTCCAGTCCCTACCCTATTGGGAAAGCC
CAGACTCAGGAGACATGGTCCAAGGAAATCCCTGACAGAAAACCGGGAGA
GGGCAGGGCTGTGGAGCCTGAAACACACCCCACACCCATGGTGACAGTCA
CTTCTCACATATGCCTAGGAACCTATCTGAAACCTTTGGCCATCTCTCTC
TGAAAAGATGAGGCTGCAAATACACACACACACACACACACACACACACA
CACACACACACACACACACACACACACACACACAAATGTCCTTCAAGCCT
TTTTGACAAGGTTTTCTGGTGGATCCCGGGGATATGAAGTTGTTCTCAGC
AGATATCTGGGAGTCTTGACTCCTGGCCCTCTGAGTAAATGGATGAAGCG
AAGAAGAATGGGGTCCTCTGAGTAACAGGTGGATCTAGAAAATCCTATAG
GAGTCACCAGGGCACGGTGGAGGAGGGTAAGGTACAGAACTAACAATAGC
CCGAGAAGGGGAAACAGCAGGAGATGATTCCAGAGACGTAGTGACCCCAA
GCTGCAAGGGAAAGCATGAGGGGCCAGCAGGAAGGCCGACATGGCAGGTT
GTCAGCTTCTAGATCGGAAGGCGGGTCACACTTGCTCTTTCTATCCTCAG
GGCCACCTCCTCGCACAAGGAGTGTCTCCTACATCAACATCATCATGCCT
TCAGTGTTTGGTACCATCTGTCTCCTGGGCATTGTGGGAAACTCCACAGT
CATTTTTGCCGTGGTGAAGAAATCCAAGCTGCACTGGTGCAGCAACGTCC
CTGACATCTTCATCATCAACCTCTCTGTGGTGGATCTGCTTTTCCTGCTG
GGCATGCCTTTCATGATCCACCAGCTCATGGGTAATGGTGTCTGGCACTT
TGGGGAAACCATGTGCACCCTCATCACAGCCATGGACGCCAACAGTCAGT
TCACCAGCACCTACATCCTGACTGCTATGGCCATTGACCGCTACTTGGCC
ACCGTCCATCCCATCTCCTCCACCAAGTTCCGGAAGCCCTCCATGGCCAC
CCTGGTGATCTGCCTCCTGTGGGCTCTCTCGTTCATTAGCATCACTCCTG
TGTGGCTCTATGCCAGGCTTATCCCCTTCCCAGGGGGTGCTGTGGGCTGTG
GCATCCGCCTACCAAACCCAGATACTGATCTTTACTGGTTCACTCTGTAT
CAGTTTTTCCTGGCCTTCGCCCTTCCGTTTGTGGTCATCACTGCTGCGTA
CGTGAAAATACTACAGCGCATGACGTCTTCGGTGGCCCCAGCCTCTCAAC
GCAGCATCCGGCTTCGGACAAAGAGGGTGACCCGCACAGCCATTGCCATC
TGTCTGGTCTTCTTTGTGTGCTGGGCGCCCTACTACGTGCTGCAGCTGAC
CCAGTTGTCCATCAGCCGCCCGACCCTCACATTCGTCTACCTGTACAATG
```

-continued

CGGCCATCAGCTTGGGCTATGCCAACAGCTGCCTCAATCCCTTTGTGTAC

ATAGTACTCTGTGAGACCTTTCGAAAACGCTTGGTGCTGTCGGTGAAGCC

CGCGGCCCAGGGGCAGCTTCGCACGGTCAGCAATGCTCAGACAGCTGACG

AGGAGAGGACAGAAAGCAAAGGCACCTGACAATCCCCCCCGGTCACCTCC

AAGTCAGGTCACCGCATCAAACCATGGGGAGAGATACTGAGATAAACCCG

GGGCTACCCTGGGAGGATGCAGAAGCTGGAGGCTGGGGGCTTGTAGCAAA

CCACATTCCACGGGGCCCACAAATTGCTAGGGAGGCTTGCAGCCTGGTTG

GGGGGGAAGCCTCAGACTGCAGGGATCCCCTTGACAGAATAGAAGCGGAG

CAAGAAGGAAAGGGTGGTTTGACTGGTTCTCGGGGTCTGTATCTGTTGGC

TCGCATATATCTTCTCTCAAGGGAAGAAGGCGGAGGTGCCTAGCTGGGTT

CCTTTAAAACTAGGCAGGGCTAGGATCTGAGCAGCTAGGGCTCTACTGTG

AGACTGGGCAAGCCGAGCGTTCCCTCCCATCTCTCATTGGTGTTGATAGA

AGGCAGTCTTTCTCCCAAGCTGGTGGATCTCCTGAAGCACGCTGCCTGGG

CTCCAGCATCCTGTGCGGATTTCACGTTCTCTTAGGGGATGCATGTTGAC

ACTGGGGTGTGGGCTCTGAGCCCACAGGAGTTTAAAAAACCAAAAGAGCT

CAGAGTGTCGAGAGAGACCCAATCACCGAGAATGACAAGGCAACCTGGGG

TGGATGTGGATCTTGAAACTAATAAAAAGGGGTTTTCACAGTGACAGCGA

CATTCTCTTCATAGGGCACAGCTGTCAGTCTATGGCTGATCCAGAGCGAG

CATCCATGAATTCTGCATGTGCAGGGGTCACTCTAATACCTGATATGTTG

GCATCATCTTTGTGCTTGAGCCTTCCNCTCCCAAATGGGAATGAAATAAA

GGCAAATTCCCNCCCCCCCCAAAAAAGGGGNAAAAAAAAAAAAAAAAAAA

AAAAAAA

Human short form/mouse species chimeric MCH1R:
SEQ. ID. NO.19

ATGGACCTGGAAGCCTCGCTGCTGCCCACTGGTCCCAATGCCAGCAACAC

CTCTGATGGCCCCGATAACCTCACTTCGGCAGGATCACCTCCTCGCACGG

GGAGCATCTCCTACATCAACATCATCATGCCTTCGGTGTTCGGCACCATC

TGCCTCCTGGGCATCATCGGGAACTCCACGGTCATCTTCGCGGTCGTGAA

GAAGTCCAAGCTGCACTGGTGCAACAACGTCCCCGACATCTTCATCATCA

ACCTCTCGGTAGTAGATCTCCTCTTTCTCCTGGGCATGCCCTTCATGATC

CACCAGCTCATGGGCAATGGGGTGTGGCACTTGGGGAGACCATGTGCACC

CTCATCACGGCCATGGATGCCAATAGTCAGTTCACCAGCACCTACATCCT

GACCGCCATGGCCATTGACCGCTACCTGGCCACTGTCCACCCCATCTCTT

CCACGAAGTTCCGGAAGCCCTCCATGGCCACCCTGGTGATCTGCCTCCTG

TGGGCTCTCTCGTTCATTAGCATCACTCCTGTGTGGCTCTATGCCAGGCT

TATCCCCTTCCCAGGGGTGCTGTGGGCTGTGGCATCCGCCTACCAAACC

CAGATACTGATCTTACTGGTTCACTCTGTATCAGTTTTTCCTGGCCTTCG

CCCTTCCGTTGTGGTCATCACTGCTGCGTACGTGAAAATACTACAGCGCA

TGACGTCTTCGGTGGCCCCAGCCTCTCAACGCAGCATCCGGCTTCGGACA

AAGAGGGTGACCCGCACAGCCATTGCCATCTGTCTGGTCTTCTTTGTGTG

CTGGGCGCCCTACTACGTGCTGCAGCTGACCCAGTTGTCCATCAGCCGCC

-continued

CGACCCTCACATTCGTCTACCTGTACAATGCGGCCATCAGCTTGGGCTAT

GCCAACAGCTGCCTCAATCCCTTGTGTACATAGTACTCTGTGAGACCTTT

CGAAAACGCTTGGTGCTGTCGGTGAAGCCCGCGGCCCAGGGGCAGCTTTC

GCACGGTCAGCAATGCTCAGACAGCTGACGAGGAGAGGACAGAAAGCAAA

GGCACCTGA

Human long form1mouse species chimeric MCH1R:
SEQ. ID. NO.20

ATGTCAGTGGGAGCCATGAAGAAGGGAGTGGGGAGGGCAGTTGGGCTTG

GAGGCGGCAGCGGCTGCCAGGCTACGGAGGAAGACCCCCTTCCCAACTG

CGGGGCTTGCGCTCCGGGACAAGQTGGCAGGCGCTGGAGGCTGCCGCAG

CCTGCGTGGGTGGAGGGGAGCTCAGCTCGGTTGTGGGAGCAGGCGACCG

GCACTGGCTGGATGGACCTGGAAGCCTCGCTGCTGCCCACTGGTCCCAA

CGCCAGCAACACCTCTGATGCCCCCGATAACCTCACTTCGGCAGGATCA

CCTCCTCGCACGGGAGCATCTCCTACATCAACATCATCATGCCTTCGG

TGTTCGGCACCATCTGCCTCCTGGGCATCATCGGGAACTCCACGGTCAT

CTTCGCGGTCGTGAAGAAGTCCAAGCTGCACTGGTGCAACAACGTCCCC

GACATCTTCATCATCAACCTCTCGGTAGTAGATCTCCTCTTTCTCCTGG

GCATGCCCTTCATGATCCACCAGCTCATGGGCAATGGGGTGTGGCACTT

TGGGGAGACCATGTGCACCCTCATCACGGCCATGGATGCCAATAGTCAG

TTCACCAGCACCTACATCCTGACCGCCATGGCCATTGACCGCTACCTGG

CCACTGTCCACCCCATCTCTTCCACGAAGTTCCGGAAGCCCTCCATGGC

CACCCTGGTGATCTGCCTCCTGTGGGCTCTCTCGTTCATTAGCATCACT

CCTGTGTGGCTCTATGCCAGGCTTATCCCCTTCCCAGGGGGTGCTGTGG

GCTGTGGCATCCGCCTACCAAACCCAGATACTGATCTTTACTGGTTCAC

TCTGTATCAGTTTTTCCTGGCCTTCGCCCTTCCGTTTGTGGTCATCACT

GCTGCGTACGTGAAAATACTACAGCGCATGACGTCTTCGGTGGCCCCAG

CCTCTCAACGCAGCATCCGGCTTCGGACAAAGAGGGTGACCCGCACAGC

CATTGCCATCTGTCTGGTCTTCTTTGTGTGCTGGGCGCCCTACTACGTG

CTGCAGCTGACCCAGTTGTCCATCAGCCGCCCGACCCTCACATTCGTCT

ACCTGTACAATGCGGCCATCAGCTTGGGCTATGCCAACAGCTGCCTCAA

TCCCTTTGTGTACATAGTACTCTGTGAGACCTTTCGAAAACGCTTGGTG

CTGTCGGTGAAGCCCGCGGCCCAGGGGCAGCTTCGCACGGTCAGCAATG

CTCAGACAGCTGACGAGGAGAGGACAGAAAGCAAAGGCACCTGA

Aequorea victoria Green Fluorescent Protein (GTP)
cDNA: Nucleic acid sequence start and stop codons
are highlighted:
SEQ. ID. NO.21

TACACACGAATAAAAGATAACAAAGATGAGTAAAGGAGAAGAACTTTTCA

CTGGAGTTGTCCCAATTCTTGTTGAATTAGATGGTGATGTTAATGGGCAC

AAATTTTCTGTCAGTGQAGAGGGTGAAGGTGATGCAACATACGGAAAACT

TACCCTTAAATTTATTTGCACTACTGGAAAACTACCTGYfCCATGGCCAA

CACTTGTCACTACTTTCTCTTATGGTGTTCAATGCTTTTCAAGATACCCA

GATCATATGAAACAGCATGACTTTTTCAAGAGTGCCATGCCCGAAGGTTAT

-continued

GTACAGGAAAGAACTATATTTTTCAAAGATGACGGGAACTACAAGACACG

TGCTGAAGTCAAGTTTTGAAGGTGATACCCTTGTTAATAGAATCGAGTTA

AAAGGTATTGATTPTAAAGAAGATGGAAACATTCTTGGACACAAATTGGA

ATACAACTATAACTCACACAATGTATACATCATGGCAGACAAACAAAAGA

ATGGAATCAAAGTTAACTTCAAAATTAGACACAACATTGAAGATGGAAGC

GTTCAACTAGCAGACCATTATCAACAAAATACTCCAATTGGCGATGGCCC

TGTCCTTTTACCAGACAACCATTACCTGTCCACACAATCTGCCCTTTCGA

AAGATCCCAACGAAAAGAGAGACCACATGGTCCTTCTTGAGTTTGTAACA

GCTGCTGGGATTACACATGGCATGGATGAACTATACAAATAAATGTCCAG

ACTTCCAATTGACACTAAAGTGTCCGAACAATTACTAAAATCTCAGGGTT

CCTGGTTAAATTCAGGCTGAGATATTTATTTATATATTTATAGATTCATTA

AAATTGTATGAATAATTTATTGATGTTATTGATAGAGGTATTTTCTTATT

AAACAGGCTACTTGGAGTGTATTCTTAATTCTATATTAATTACAATTTGA

TTTGACTTGCTCAAA

EGEP + Linker Nucleic acid sequence start and stop
codons are highlighted and a 12 amino acid linker
sequence is denoted in lower case:

SEQ. ID. NO.22 gtcgacggtaccgcgggcccgggatccatcgccaccATGGTGAGCAAGGG

CGAGGAGCTGTTCACCGGGQTGGTGCCCATCCTGGTCGAGCTGGACGGCG

ACGTAAACGGCCACAAGTTCAGCGTGTCCGGCGAGGGCGAGGGCGATGCC

ACCTACGGCAAGCTGACCCTGAAGTTCATCTGCACCACCGGCAAGCTGCC

CGTGCCCTGGCCCACCCTCGTGACCACCCTGACCTACGGCGTGCAGTGCT

TCAGCCGCTACCCCGACCACATGAAGCAGCACGACTTCTTCAAGTCCGCC

ATGCCCGAAGGCTACGTCCAGGAGCGCACCATCTTCTTCAAGGACGACGG

CAACTACAAGACCCGCGCCGAGGTGAAGTTCGAGGGCGACACCCTGGTGA

ACCGCATCGAGCTGAAGGGCATCGACTTCAAGGAGGACGGCAACATCCTG

GGGCACAAGCTGGAGTACAACTACAACAGCCACAACGTCTATATCATGGC

CGACAAGCAGAAGAACGGCATCAAGGTGAACTTCAAGATCCGCCACAACA

TCGAGGACGGCAGCGTGCAGCTCGCCGACCACTACCAGCAGAACACCCCC

ATCGGCGACGGCCCCGTGCTGCTGCCCGACAACCACTACCTGAGCACCCA

GTCCGCCCTGAGCAAAGACCCCAACGAGAAGCGCGATCACATGGTCCTGC

TGGAGTTCGTGACCGCCGCCGGGATCACTCTCGGCATGGACGAGCTGTAC

AAGTAAAGCGGCCGC

Emerald:

SEQ. ID. NO.23

ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCTTGACCTA

CGGCGTGCAGTGCTTCGCCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

-continued

CGACACCCTGGTGAACCGCATCGAGCTGAAGGGCATCGACTTCAAGGAGG

ACGGCAACATCCTGGGGCACAAGCTGGAGTACAACTACAACAGCCACAAG

GTCTATATCACCGCCGACAAGCAGAAGAACGGCATCAAGGTGAACTTCAA

GACCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA

Topaz:

SEQ. ID. NO.24

ATGGTGAGCAAGGGCGAGGAGGAGCTGTTCACCGGGGTGGTGCCCATCCT

GGTCGAGCTGGACGGCGACGTAAACGGCCACAAGTTCAGCGTGTCCGGCG

AGGGCGAGGGCGATGCCACCTACGGCAAGCTGACCCTGAAGTTCATCTGC

ACCACCGGCAAGCTGCCCGTGCCCTGGCCCACCCTCGTGACCACCTTCGG

CTACGGCGTGCAGTGCTTCGCCCGCTACCCCGACCACATGCGCCAGCACG

ACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGA

GGGCGACACCCTGGTGAACCGCATCGAGCTGAAGGGCATCGACTTCAAGG

AGGACGGCAACATCCTGGGGCACAAGCTGGAGTACAACTACAACAGCCAC

AACGTCTATATCATGGCCGACAAGCAGAAGAACGGCATCAAGGTGAACTT

CAAGATCCGCCACAACATCGAGGACGGCAGCGTGCAGCTCGCCGACCACT

ACCAGCAGAACACCCCCATCGGCGACGGCCCCGTGCTGCTGCCCGACAAC

CACTACCTGAGCTACCAGTCCGCCCTGAGCAAAGACCCCAACGAGAAGCG

CGATCACATGGTCCTGCTGGAGTTCGTGACCGCCGCCGGGATCACTCTCG

GCATGGACGAGCTGTACAAGTAA

W1B:

SEQ. ID. NO.25

ATGGTGAGCAAGGGCGAGGAGCTGTTTCACCGGGGTGGTGCCCATCCTGG

TCGAGCTGGACGGCGACGTAAACGGCCACAGGTTCAGCGTGTCCGGCGAG

GGCGAGGGCGATGCCACCTACGGCAAGCTGACCCTGAAGTTCATCTGCAC

CACCGGCAAGCTGCCCGTGCCCTGGCCCACCCTCGTGACCACCCTGACCT

GGGGCGTGCAGTGCTTCAGCCGCTACCCCGACCACATGAAGCAGCACGAC

TTCTTCAAGTCCGCCATGCCCGAAGGCTACGTCCAGGAGCGTACCATCTT

CTTCAAGGACGACGGCAACTACAAGACCCGCGCCGAGGTGAAGTTCGAGG

GCGACACCCTGGTGAACCGCATCGAGCTGAAGGGCATCGACTTCAAGGAG

GACGGCAACATCCTGGGGCACAAGCTGGAGTACAACTACATCAGCCACAA

CGTCTATATCACCGCCGACAAGCAGAAGAACGGCATCAAGGCCCACTTCA

AGATCCGCCACAACATCGAGGACGGCAGCGTGCAGCTCGCCGACCACTAC

CAGCAGAACACCCCCATCGGCGACGGCCCCGTGCTGCTGCCCGACAACCA

CTACCTGAGCACCCAGTCCGCCCTGAGCAAAGACCCCAACGAGAAGCGCG

ATCACATGGTCCTGCTGGAGTTCGTGACCGCCGCCGGGATCACTCTCGGC

ATGGACGAGCTGTACAAGTAA

-continued

Mouse MCH1R-linker-EGFP: Nucleic acid sequence start codon and start and stop codons for mouse MCH1R and EGFP, respectively, as well as intron borders, are highlighted and a 12 amino acid linker sequence is denoted in lower case:

SEQ. ID. NO.26

ATGGATCTGCAAGCCTCGTTGCTGTCCACTGGCCCCAATGCCAGCAACAT
CTCCGATGGCCAGGATAATTTCACATTGGCGGGTGAGTCGAGTTGGAGTC
CTCCCTCCTCCGGGATGGGTGTGGAAAATGGGAAGGTTTCACCTCCCAAG
CCAAACTGCCTGGGAAACTTTATCTTACAGTTCTTGGTGATAAGATCTGC
AGTCGGCTTTGCCTGAAGAGGAAGAGGAGAGGAGGGGACACCAGCTAGGA
CAGAAGGGGCAGGGAGGAATAGAGATGGGGCAGAGGCACATTTAGAAACA
ACAAGGGTTGGTGACAAGACGTGAGGCAGGCTTGAGGGGAAAGCTTGCTG
ATGAGTCCCAAATATGCTTTGCAGGGGGGGGGGGGGGAATCAAGGCTG
GAGAAGCAAGCAAGCAAGACAGCAAGACAGCGGGCGGGTAGTATGTGGGA
GCCAGCAGAAGCGCTTTGATTCACCGCTATCCTGGGCTCAATCCTCTGGC
CTCGCACTGGGGAAATGGGGTCTGAGTGGTCCTGCTGTCTTCTGGCAAAG
GCTGCTGGGAGCAAAAGACTTCACAGGGCGTGAGAGGATfAACTTTTCTG
GTGAATTAAGCTTCTTGACATTTGCAGAACGTCAATGCCTTAAAATTCTA
GCTCTGAAGGAGAAGGGAATGAAGGGGAAAGAGGGAAGGTTGGTGTGGAG
AAATTCCCAAGCTTCTGGGGTGTAACACAGCTCCAGTCCCTACCCTATTG
GGAAAGCCCAGACTCAGGAGACATGGTCCAAGGAAATCCCTGACAGAAAA
CCGGGAGAGGGCAGGGCTGTGGAGCCTGAAACACACCCCACACCCATGGT
GACAGTCACTTCTCACATATGCCTAGGAACCTATCTGAAACCTTTGGCCA
TCTCTCTCTGAAAAGATGAGGCTGCAAATACACACACACACACACACACA
CACACACACACACACACACACACACACACACACACACACACAAATGTCCT
TCAAGCCTTTTGACAAGGTTTTCTGGTGGATCCCGGGGATATGAAGTTGT
TCTCAGCAGATATCTGGGAGTCTTGACTCCTGGCCCTCTGAGTAAATGGA
TGAAGCGAAGAAGAATGGGGTCCTCTGAGTAACAGGTGGATCTAGAAAAT
CCTATAGGAGTCACCAGGGCACGGTGGAGGAGGGTAAGGTACAGAACTAA
CAATAGCCCGAGAAGGGGAAACAGCAGGAGATGATTCCAGAGACGTAGTG
ACCCCAAGCTGCAAGGGAAAGCATGAGGGGCCAGCAGGAAGGCCGACATG
GCAGGTTGTCAGCTTCTAGATCGGAAGGCGGGTCACACTTGCTCTTCTAT
CCTCAGGGCCACCTCCTCGCACAAGGAGTGTCTCCTACATCAACATCATC
ATGCCTTCAGTGTTGGTACCATCTGTCTCCTGGGCATTGTGGGAAACTCC
ACAGTCATPTTTGCCGTGGTGAAGAAATCCAAGCTGCACTGGTGCAGCAA
CGTCCCTGACATCTTCATCATCAACCTCTCTGTGGTGGATCTGCTTTCCT
GCTGGGCATGCCTTTCATGATCCACCAGCTCATGGGTAATGGTGTCTGGC
ACTTTGGGGAAACCATGTGCACCCTCATCACAGCCATGGACGCCAACAGT
CAGTTCACCAGCACCTACATCCTGACTGCTATGGCCATTGACCGCTACTT
GGCCACCGTCCATCCCATCTCCTCCACCAAGTTCCGGAAGCCCTCCATGG
CCACCCTGGTGATCTGCCTCCTGTGGGCTCTCTCGTTCATTAGCATCACT
CCTGTGTGGCTCTATGCCAGGCTTATCCCCTTCCCAGGGGGTGCTGTGGG

-continued

CTGTGGCATCCGCCTACCAAACCCAGATACTGATCTTACTGGTTCACTCT
GTATCAGTTTTTCCTGGCCTTCGCCCTTCCGTTTGTGGTCATCACTGCTG
CGTACGTGAAAATACTACAGCGCATGACGTCTTCGGTGGCCCCAGCCTCT
CAACGCAGCATCCGGCTTCGGACAAAGAGGGTGACCCGCACAGCCATTGC
CATCTGTCTGGTCTTCTTTGTGTGCTGGGCGCCCTACTACGTGCTGCAGC
TGACCCAGTTGTCCATCAGCCGCCCGACCCTCACATTCGTCTACCTGTAC
AATGCGGCCATCAGCTTGGGCTATGCCAACAGCTGCCTCAATCCCTTTGT
GTACATAGTACTCTGTGAGACCTTTCGAAAACGCTTGGTGCTGTCGGTGA
AGCCCGCGGCCCAOGGGCAGCTTCGCACGGTCAGCAATGCTCAGACAGCT
GACGAGGAGAGGACAGAAAGCAAAGGCACCgtcgacggtaccgcgggccc
gggatccatcgccaccATGGTGAGCAAGGGCGAGGAGCTGTTCACCGGGG
TGGTGCCCATCCTGGTCGAGCTGGACGGCGACGTAAACGGCCACAAGTTC
AGCGTGTCCGGCGAGGGCGAGGGCGATGCCACCTACGGCAAGCTGACCCT
GAAGYfCATCTGCACCACCGGCAAGCTGCCCGTGCCCTGGCCCACCCTCG
TGACCACCCTGACCTACGGCGTGCAGTGCTTCAGCCGCTACCCCGACCAC
ATGAAGCAGCACGACTTCTTCAAGTCCGCCATGCCCGAAGGCTACGTCCA
GGAGCGCACCATCTTCTTCAAGGACGACGGCAACTACAAGACCCGCGCCG
AGGTGAAGTTCGAGGGCGACACCCTGGTGAACCGCATCGAGCTGAAGGGC
ATCGACTTCAAGGAGGACGGCAACATCCTGGGGCACAAGCTGGAGTACAA
CTACAACAGCCACAACGTCTATATCATGGCCGACAAGCAGAAGAACGGCA
TCAAGGTGAACTTCAAGATCCGCCACAACATCGAGGACGGCAGCGTGCAG
CTCGCCGACCACTACCAGCAGAACACCCCCATCGGCGACGGCCCCGTGCT
GCTGCCCGACAACCACTACCTGAGCACCCAGTCCGCCCTGAGCAAAGACC
CCAACGAGAAGCGCGATCACATGGTCCTGCTGGAGTTCGTGACCGCCGCC
GGGATCACTCTCGGCATGGACGAGCTGTACAAGTAA Mouse MCH1R/EGFP direct fusion: Nucleic acid sequence start codon and start and stop codons for mouse MCH1R and EGFP, respectively, as well as intron borders, are highlighted:

SEQ. ID. NO.27

ATGGATCTGCAAGCCTCGTTGCTGTCCACTGCCCCAATGCCAGCAACATC
TCCGATGGCCAGGATAATTTCACATTGGCGGGTGAGTCGAGTTGGAGTCC
TCCCTCCTCCGGGATGGGTGTGGAAAATGGGAAGGTTTCACCTCCCAAGC
CAAACTGCCTGGGAAACTTTATCTTACAGTTCTTGGTGATAAGATCTGCA
GTCGGCTTTGCCTGAAGAGGAAGAGGAGAGGAGGGGACACCAGCTAGGAC
AGAAGGGGCAGGGAGGAATAGAGATGGGGCAGAGGCACATTTAGAAACAA
CAAGGGTTGGTGACAAGACGTGAGGCAGGCTTGAGGGGAAAGCTTGCTGA
TGAGTCCCAAATATGCTTTGCAGGGGGGGGGGGGGGAATCAAGGCTGG
AGAAGCAAGCAAGCAAGACAGCAAGACAGCGGGCGGGTAGTATGTGGGAG
CCAGCAGAAGCGCTTTGATTCACCGCTATCCTGGGCTCAATCCTCTGGCC
TCGCACTGGGGAAATGGGGTCTGAGTGGTCCTTGCTGTCTTCTGGCAAAG
GCTGCTGGGAGCAAAAGACTTCACAGGGCGTGAGAGGATTAACTTTTCTG
GTGAATTAAGCTTCTTGACATTTGCAGAACGTCAATGCCTTAAAATTCTA

-continued

GCTCTGAAGGAGAAGGGAATGAAGGGGAAAGAGGGAAGGTTGGTGTGGAG

AAATTCCCAAGCTTCTGGGGTGTAACACAGCTCCAGTCCCTACCCTATTG

GGAAAGCCCAGACTCAGGAGACATGGTCCAAGGAAATCCCTGACAGAAAA

CCGGGAGAGGGCAGGGCTGTGGAGCCTGAAACACACCCCACACCCATGGT

GACAGTCACTTCTCACATATGCCTAGGAACCTATCTGAAACCTTTGGCCA

TCTCTCTCTGAAAAGATGAGGCTGCAAATACACACACACACACACACACA

CACACACACACACACACACACACACACACACACACACACACAAATGTCCT

TCAAGCGTTTTTGACAAGGTTTTCTGGTGGATCCCGGGGATATGAAGTTG

TTCTCAGCAGATATCTGGGAGTCTTGACTCCTGGCCCTCTGAGTAAATGG

ATGAAGCGAAGAAGAATGGGGTCCTCTGAGTAACAGGTGGATCTAGAAAA

TCCTATAGGAGTCACCAGGGCACGGTGGAGGAGGGTAAGGTACAGAACTA

ACAATAGCCCGAGAAGGGGAAACAGCAGGAGATGATTCCAGAGACGTAGT

GACCCCAAGCTGCAAGGGAAAGCATGAGGGGCCAGCAGGAAGGCCGACAT

GGCAGGTTGTCAGCTTCTAGATCGGAAGGCGGGTCACACTTGCTCTTTCT

ATCCTCAGGGCCACCTCCTCGCACAAGGAGTGTCTCCTACATCAACATCA

TCATGCCTTUCAGTGTTGGTACCATCTGTCTCCTGGGCATTGTGGGAAAC

TCCACAGTCATLTPTGCCGTGGTGAAGAAATCCAAGCTGCACTGGTGCAG

CAACGTCCCTGACATCTTCATCATCAACCTCTCTGTGGTGGATCTGCTTT

CCTGCTGGGCATGCCTTTCATGATCCACCAGCTCATGGGTAATGGTGTCT

GGCACTTTGGGGAAACCATGTGCACCCTCATCACAGCCATGGACGCCAAC

AGTCAGTTCACCAGCACCTACATCCTGACTGCTATGGCCATTGACCGCTA

CTTGGCCACCGTCCATCCCATCTCCTCCACCAAGTTCCGGAAGCCCTCCA

TGGCCACCCTGGTGATCTGCCTCCTGTGGGCTCTCTCGTTCATTAGCATC

ACTCCTGTGTGGCTCTATGCCAGGCTTATCCCCTTCCCAGGGGGTGCTGT

GGGCTGTGGCATCCGCCTACCAAACCCAGATACTGATCTTACTGGTTCAC

TCTGTATCAGTTTTTCCTGGCCTTCGCCCTTCCGTTTGTGGTCATCACTG

CTGCGTACGTGAAAATACTACAGCGCATGACGTCTTCGGTGGCCCCAGCC

TCTCAACGCAGCATCCGGCTTCGGACAAAGAGGGTGACCCGCACAGCCAT

TGCCATCTGTCTGGTCTTCTLTGTGTGCTGGGCGCCCTACTACGTGCTGC

AGCTGACCCAGTTGTCCATCAGCCGCCCGACCCTCACATTCGTCTACCTG

TACAATGCGGCCATCAGCTTGGGCTATGCCAACAGCTGCCTCAATCCCTT

TGTGTACATAGTACTCTGTGAGACCTTCGAAAACGCTTGGTGCTGTCGGT

GAAGCCCGCGGCCCAGGGGCAGCTTCGCACGGTCAGCAATGCTCAGACAG

CTGACGAGGAGAGGACAGAAAGCAAAGGCACCATGGTGAGCAAGGGCGAG

GAGCTGTTCACCGGGGTGGTGCCCATCCTGGTCGAGCTGGACGGCGACGT

AAACGGCCACAAGTTCAGCGTGTCCGGCGAGGGCGAGGGCGATGCCACCT

ACGGCAAGCTGACCCTGAAGTTCATCTGCACCACCGGCAAGCTGCCCGTG

CCCTGGCCCACCCTCGTGACCACCCTGACCTACGGCGTGCAGTGCTTCAG

CCGCTACCCCGACCACATGAAGCAGCACGACTTCTTCAAGTCCGCCATGC

CCGAAGGCTACGTCCAGGAGCGCACCATCTTCTTCAAGGACGACGGAACT

-continued

ACAAGACCCGCGCCGAGGTGAAGTTCGAGGGCGACACCCTGGTGAACCGC

ATCGAGCTGAAGGGCATCGACTTCAAGGAGGACGGCAACATCCTGGGGCA

CAAGCTGGAGTACAACTACAACAGCCACAACGTCTATATCATGGCCGACA

AGCAGAAGAACGGCATCAAGGTGAACTTCAAGATCCGCCACAACATCGAG

GACGGCAGCGTGCAGCTCGCCGACCACTACCAGCAGAACACCCCCATCGG

CGACGGCCCCGTGCTGCTGCCCGACAACCACTACCTGAGCACCCAGTCCG

CCCTGAGCAAAGACCCCAACGAGAAGCGCGATCACATGGTCCTGCTGGAG

TTCGTGACCGCCGCCGGGATCACTCTCGGCATGGACGAGCTGTACAAGTA

A

Human short form/mouse species chinieric MCH1R-
linker-EGFP: Nucleic acid sequence start codon and
start and stop codons for mouse MCH1R and BGTP,
respectively, are highlighted and a 12 amino acid
linker sequence is denoted in lower case:
SEQ. ID. NO.28

ATGGACCTGGAAGCCTCGCTGCTGCCCACTGGTCCCAATGCCAGCAACAC

CTCTGATGGCCCCGATAACCTCACTTCGGCAGGATCACCTCCTCGCACGG

GGAGCATCTCCTACATCAACATCATCATGCCTTCGGTGTTCGGCACCATC

TGCCTCCTGGGCATCATCGGGAACTCCACGGTCATCTTCGCGGTCGTGAA

GAAGTCCAAGCTGCACTGGTGCAACAACGTCCCCGACATCTTCATCATCA

ACCTCTCGGTAGTAGATCTCCTCTPTCTCCTGGGCATGCCCTTCATGATC

CACCAGCTCATGGGCAATGGGGTGTGGCACTTGGGGAGACCATGTGCACC

CTCATCACGGCCATGGATGCCAATAGTCAGTTTCACCAGCACCTACATCC

TGACCGCCATGGCCATTGACCGCTACCTGGCCACTGTCCACCCCATCTCT

TCCACGAAGTTCCGGAAGCCCTCCATGGCCACCCTGGTGATCTGCCTCCT

GTGGGCTCTCTCGTTCATTAGCATCACTCCTGTGTGGCTCTATGCCAGGC

TTATCCCCTPCCCAGGGGGTGCTGTGGGCTGTGGCATCCGCCTACCAAAC

CCAGATACTGATCTTTACTGG1TTCACTCTGTATCAGTTTTTCCTGGCCT

TCGCCCTTCCGTTTGTGGTCATCACTGCTGCGTACGTGAAAATACTACAG

CGCATGACGTCTTCGGTGGCCCCAGCCTCTCAACGCAGCATCCGGCTTCG

GACAAAGAGGGTGACCCGCACAGCCATTGCCATCTGTCTGGTCTTCTTTG

TGTGCTGGGCGCCCTACTACGTGCTGCAGCTGACCCAGTTGTCCATCAGC

CGCCCGACCCTCACATTCGTCTACCTGTACAATGCGGCCATCAGCTTGGG

CTATGCCAACAGCTGCCTCAATCCCTffGTGTACATAGTACTCTGTGAGA

CCTTTCGAAAACGCTTGGTGCTGTCGGTGAAGCCCGCGGCCCAGGGGCAG

CTTCGCACGGTCAGCAATGCTCAGACAGCTGACGAGGAGAGGACAGAAAG

CAAAGGCACCgtcgacggtaccgcgggcccgggatccatcgccaccATGG

TGAGCAAGGGCGAGGAGCTGTTCACTGGGGTGGTGCCCATCCTGGTCGAG

CTGGACGGCGACGTAAACGGCCACAAGTTCAGCGTGTCCGGCGAGGGCGA

GGGCGATGCCACCTACGGCAAGCTGACCCTGAAGTTCATCTGCACCACCG

GCAAGCTGCcCGTGCCCTGGCCCACCCTCGTGACCACCCTGACCTACGGC

GTGCAGTGCTTCAGCCGCTACCCCGACCACATGAAGCAGCACGACTTCTT

CAAGTCCGCCATGCCCGAAGGCTACGTCCAGGAGCGCACCATCTTCTTCA

```
AGGACGACGGCAACTACAAGACCCGCGCCGAGGTGAAGTTCGAGGGCGAC

ACCCTGGTGAACCGCATCGAGCTGAAGGGCATCGACTTCAAGGAGGACGG

CAACATCCTGGGGCACAAGCTGGAQTACAACTACAACAGCCACAACGTCT

ATATCATGGCCGACAAGCAGAAGAACGGCATCAAGGTGAACTTCAAGATC

CGCCACAACATCGAGGACGGCAGCGTGCAGCTCGCCGACCACTACCAGCA

GAACACCCCATCGGCGACGGCCCCGTGCTGCTGCCCGACAACCACTACC

TGAGCACCCAGTCCGCCCTGAGCAAAGACCCCAACGAGAAGCGCGATCAC

ATGGTCCTGCTGGAGTTCGTGACCGCCGCCGGGATCACTCTCGGCATGGA

CGAGCTGTACAAGTAA

Human long form/mouse species chimeric MCH1R-link-
er-EGFP: Nucleic acid sequence start codon and
start and stop codons for mouse MCH1R and EGFP,
respectively, are highlighted and a 12 amino acid
linker sequence is denoted in lower case:
                                    SEQ. ID. NO.29
ATGTCAGTGGGAGCCATGAAGAAGGGAGTGGGGAGGGCAGTTGGGCTTGG

AGGCGGCAGCGGCTGCCAGGCTACGGAGGAAGACCCCCTTCCCAACTGCG

GGGCTTGCGCTCCGGGACAAGGTGGCAGGCGCTGGAGGCTGCCGCAGCCT

GCGTGGGTGGAGGGGAGCTCAGCTCGGTTGTGGGAGCAGGCGACCGGCAC

TGGCTGGATGGACCTGGAAGCCTCGCTGCTGCCCACTGGTCCCAACGCCA

GCAACACCTCTGATGGCCCCGATAACCTCACTTCGGCAGGATCACCTCCT

CGCACGGGGAGCATCTCCTACATCAACATCATCATGCCTTCGGTGTTCGG

CACCATCTGCCTCCTGGGCATCATCGGGAACTCCACGGTCATCTTCGCGG

TCGTGAAGAAGTCCAAGCTGCACTGGTGCAACAACGTCCCCGACATCTTC

ATCATCAACCTCTCGGTAGTAGATCTCCTCTTTCTCCTGGGCATGCCCTT

CATGATCCACCAGCTCATGGGCAATGGGGTGTGGCACTTTGGGGAGACCA

TGTGCACCCTCATCACGGCCATGGATGCCAATAGTCAGTTCACCAGCACC

TACATCCTGACCGCCATGGCCATTGACCGCTACCTGGCCACTGTCCACCC

CATCTCTTCCACGAAGTTCCGGAAGCCCTCCATGGCCACCCTGGTGATCT

GCCTCCTGTGGGCTCTCTCGTTCATTAGCATCACTCCTGTGTGGCTCTAT

GCCAGGCTTATCCCCTTCCCAGGGGGTGCTGTGGGCTGTGGCATCCGCCT

ACCAAACCCAGATACTGATCTTACTGGTTCACTCTGTATCAGTTTTTCCT

GGCCTTCGCCCTTCCGTTTGTGGTCATCACTGCTGCGTACGTGAAAATAC

TACAGCGCATGACGTCTTCGGTGGCCCCAGCCTCTCAACGCAGCATCCGG

CTTCGGACAAAGAGGGTGACCCGCACAGCCATTGCCATCTGTCTGGTCTT

CTTTGTGTGCTGGGCGCCCTACTACGTGCTGCAGCTGACCCAGTTGTCCA

TCAGCCGCCCGACCCTCACATTCGTCTACCTGTACAATGCGGCCATCAGC

TTGGGCTATGCCAACAGCTGCCTCAATCCCTTGTGTACATAGTACTCTGT

GAGACCTTCGAAAACGCTTGGTGCTGTCGGTGAAGCCCGCGGCCCAGGGG

CAGTTCGCACGGTCAGCAATGCTCAGACAGCTGACGAGGAGAGGACAGAA

AGCAAAGGCACCgtcgacggtaccgcgggcccgggatccatcgccaccAT

GGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGC

GAGGGCGATGCCACCTACGGCAAGCTGACCCTGAAGTTCATCTGCACCAC

CGGCAAGCTGCCCGTGCCCTGGCCCACCCTCGTGACCACCCTGACCTACG

GCGTGCAGTGCTTCAGCCGCTACCCCGACCACATGAAGCAGCACGACTTC

TTCAAGTCCGCCATGCCCGAAGGCTACGTCCAGGAGCGCACCATCTTCTT

CAAGGACGACGGCAACTACAAGACCCGCGCCGAGGTGAAGTTCGAGGGCG

ACACCCTGGTGAACCGCATCGAGCTGAAGGGCATCGACTTCAAGGAGGAC

GGCAACATCCTGGGGCACAAGCTGGAGTACAACTACAACAGCCACAACGT

CTATATCATGGCCGACAAGCAGAAGAACGGCATCAAGGTGAACTTCAAGA

TCCGCCACAACATCGAGGACGGCAGCGTGCAGCTCGCCGACCACTACCAGC

AGAACACCCCCATCGGCGACGGCCCCGTGCTGCTGCCCGACAACCACTAC

CTGAGCACCCAGTCCGCCCTGAGCAAAGACCCCAACGAGAAGCGCGATCA

CATGGTCCTGCTGGAGTTCGTGACCGCCGCCGGGATCACTCTCGGCATGG

ACGAGCTGTACAAGTAA
```

Example 2

Generation of Chimeric and Fusion Proteins

DNA vectors encoding fusion proteins between a MCH-R receptor (MCH1R) and several different superbright variants of Green Fluorescent Protein (GFP) were generated. GFP variants were fused either via a 12 amino acid linker: TCGACGGTACCGCGGGCCCGGGATCCATCGCCACC (SEQ. ID. NO. 30), amino acid sequence: VDGTAGPG-SIAT (SEQ. ID. NO. 31) (linker fusions) or directly to the C-terminus of MCH1R (direct fusions).

Mouse MCH1R-linker-GFP Variant Fusion Constructs

Initially, mouse MCH1R was fused in frame via the linker to Enhanced Green Fluorescent Protein (EGFP). MCH1R was PCR-amplified (95° C. for 5 minutes; 95° C. for 30 seconds, 60° C. for 45 seconds, 68° C. for 3.5 minutes, for 15 cycles; 68° C. for 7 minutes) from a full-length mouse MCH1R genomic DNA lambda clone utilizing a high fidelity polymerase mix (Expand High Fidelity PCR System from Boehringer Mannheim) and PCR primers [MCH1R (Eco RI) 5': GCGAATTCACCATGGATCTGCAAGC-CTCG (SEQ. ID. NO. 32), MCH1R (Sal I) 3': GCGTC-GACGGTGCCTTTGCTTTCTGTCC (SEQ. ID. NO. 33)] that generated Eco RI and Sal I enzymatic restriction sites at the N- and C-terminus, respectively. The MCH1R N-terminal PCR primer was also designed to introduce a Kozak consensus sequence for translation which contained an Nco I site (5'-ACCATGG-3'), and the MCH1R C-terminal PCR primer was also designed to eliminate the endogenous stop codon present in the mouse MCH1R gene. The resulting PCR product was phenol/chloroform extracted, restriction digested with Eco RI and Sal I, gel purified, and subcloned in frame into the multicloning site of Clontech's pEGFP-N3 vector between Eco RI and Sal I sites. Several resulting clones for this construct were sequenced to identify a clone with an entirely correct nucleotide sequence. This clone was named mMCH1R-1-EGFP for mouse MCH1R-linker-EGFP.

An approximately 760 bp Sal I to Not I fragment of mMCH1R-1-EGFP was excised, gel purified, and subcloned into the multicloning site of pBluescript (SK+) (Stratagene) between Sal1 and Not I sites. An approximately 710 bp Nco I to Bsr G1 fragment of EGFP was excised from the resulting pBluescript-EGFP vector and replaced with the corresponding Nco I to Bsr G1 fragment of either Emerald, Topaz, or W1B (other superbright GFP variants), which were excised from vectors pRSET-Emerald, pRSET-Topaz, and pRSET-W1B, respectively. pRSET-Emerald, pRSET-Topaz, and pRSET-W1B were obtained from Aurora Biosciences Co. Sal I to Not I fragments containing either Emerald, Topaz, or W1B were excised from the resulting pBluescript-Emerald, pBluescript-Topaz, and pBluescript-W1B vectors, respectively. Appropriate fragments were gel purified and subcloned into mMCH1R- 1-EGFP digested with Sal I and Not I, replacing the Sal I to Not I EGFP fragment with the corresponding Sal I to Not I fragment from either Emerald, Topaz, or W1B. Several clones for each construct were sequenced to confirm the presence of the appropriate GFP variant. The resulting vectors were named mMCH1R-1-Emerald, mMCH1R-1-Topaz, and mMCH1R-1-W1B for mouse MCH1R-linker-Emerald, mouse MCH1R-linker-Topaz, and mouse MCH1R-linker-W1B, respectively.

Mouse MCH1R/GFP Variant Direct Fusion Constructs

A two step PCR strategy was employed to generate the direct fusion constructs. First, mouse MCH1R, EGFP, and Emerald were PCR-amplified from a full-length mouse MCH1R genomic DNA lambda clone, Clontech's pEGFP-N3 vector, and Aurora's pRSET-Emerald vector, respectively. Mouse MCH1R was PCR-amplified according to the previously mentioned conditions utilizing the same N-terminal PCR primer [MCH1R (Eco RI) 5': GCGAATTCAC-CATGGATCTGCA AGCCTCG (SEQ. ID. NO. 32)], but in this case a different C-terminal PCR primer was employed. The C-terminal PCR primer [MCH1R (EGFP/Emerald) 3': CCTTGCTCACCATGGTGCCTTTGCTTTCTGTCC (SEQ. ID. NO. 34)] eliminated the endogenous stop codon of mouse MCH1R as before and introduced a region of nucleotide sequence complementary to the nucleotide sequence of the N-terminus of EGFP.

EGFP and Emerald were PCR-amplified (95° C. for 5 minutes; 95° C. for 30 seconds, 60° C. for 45 seconds, 68° C. for 1.5 minutes, for 15 cycles; 68° C. for 7 minutes) separately with a high fidelity polymerase mix (Advantage HF-2 from Clontech) from their respective templates utilizing a common N-terminal PCR primer [EGFP/Emerald (MCH1R) 5': CAGAAAGCAAAGGCACCATGGTGAG-CAA GGGCGAGGAGC (SEQ. ID. NO. 35)] that generated a region of nucleotide sequence complementary to the C-terminus of mouse MCH1R and C-terminal PCR primers [EGFP 3': GGCGGATCCTCTAGAGTCGCGGCC (SEQ. ID. NO. 36), or Emerald (EGFP) 3': GCTCTA-GAGTCGCGGCCGCTTACTTGTACAGCTCGTCC (SEQ. ID. NO. 37)] that generated a Not I site at the C-terminus. The resulting PCR products were electrophoresed on an agarose gel and the appropriate fragments were gel purified.

In a second PCR step, PCR reactions were set up between the previously generated mouse MCH1R and EGFP, or mouse MCH1R and Emerald PCR products. Following an initial 5 minute denaturation step at 95° C., two rounds of thermocycling (95° C. for 30 seconds, 60° C. for 45 seconds, 68° C. for 4 minutes) were performed in the absence of PCR primers. This allowed the mouse MCH1R and GFP variants to anneal at their complementary regions and to be filled in by the high fidelity polymerase mix Expand High Fidelity PCR System from Boehringer Mannheim), yielding double stranded template DNA.

Subsequently, the common N-terminal mouse MCH1R [MCH1R (Eco RI) 5': GCGAATTCACCATGGATCTG-CAAGCCTCG (SEQ. ID. NO. 32)] and appropriate C-terminal PCR primers [EGFP 3': GGCGGATCCTCTA-GAGTC GCGGCC (SEQ. ID. NO. 36) or Emerald (EGFP) 3': GCTCTAGAGTCGCGG CCGCTTACTTGTA-CAGCTCGTCC (SEQ. ID. NO. 37)] were added to the reactions and thermocycling was continued for an additional fifteen cycles followed by a final extension at 68° C. for 7 minutes. The resulting PCR products were phenol/chloroform extracted, restriction digested with Eco RI and Not I, electrophoresed on an agarose gel, and appropriate fragments were gel purified.

These Eco RI to Not I fragments represent direct fusions between either mouse MCH1R and EGFP, or mouse MCH1R and Emerald. Clontech's pEGFP-N3 vector was restriction digested with Eco RI and Not I liberating an approximately 780 bp Eco RI to Not I EGFP fragment. This restriction digest was electrophoresed on an agarose gel and the approximately 3.9 Kb pEGFP-N3 vector backbone was gel purified. Eco RI to Not I mouse MCH1R/EGFP or mouse MCH1R/Emerald direct fusion fragments were subcloned into the pEGFP-N3 vector backbone between Eco RI and Not I sites. Several resulting clones for each of these two constructs were sequenced to identify clones with correct nucleotide sequence; however, no clones with entirely correct nucleotide sequences were identified. Fortunately, several clones for each of the two constructs only had nucleotide mismatches in the intron region of mouse MCH1R, and therefore, were not expected to effect the functionality of the resulting fusion proteins. These clones were named mMCH1R/EGFP and mMCH1R/Emerald for mouse MCH1R/EGFP direct fusion and mouse MCH1R/Emerald direct fusion, respectively.

Human Short and Long Form/Mouse Species Chimeric MCH1R-linker-GFP Variant Fusion Constructs The initial mouse MCH1R-linker-GFP variant fusion constructs were modified to generate both human short form and human long form/mouse species chimeric MCH1R-linker-GFP variant fusion constructs. An approximately 1.7 kb Hind III to Bsp EI fragment of the mouse MCH1R gene containing exon 1, the intron, and 127 amino acids of exon 2 was excised from the various mouse MCH1R-linker-GFP variant fusion constructs and replaced by either an approximately 470 bp Hind III to Bsp EI fragment from the wild-type human MCH1R short form or an approximately 670 bp Hind III to Bsp EI fragment from the wild-type human MCH1R long form.

Several clones for each construct were sequenced to confirm the presence of the N-terminal region of either the human MCH1R short or long forms. These clones were named hshort/mMCH1R-1-GFP variant or hlong/mMCH1R-1-GFP variant for human short form/mouse species chimeric MCH1R-linker-GFP variant and human long form/mouse species chimeric MCH1R-linker-GFP variant, respectively.

Example 3

Functional Evaluation of MCH1R/GFP Variant Fusion Proteins

Both HEK293 Aequorin (National Institutes of Health) and CHO mammalian cell lines were transiently transfected with the various MCH1R/GFP variant fusion constructs, as well as the appropriate control constructs. Transfection was performed using Lipofectamine 2000 (Gibco BRL) per the manufacturer recommended protocol. Approximately 48 hours after transfection cells were harvested, stimulated with various concentrations of human MCH, and assayed for either aequorin bioluminescence (HEK293 Aequorin cells) or cAMP production (CHO cells). Aequorin bioluminescence is a representative measure of intracellular $Ca^{2+}$ mobilization. cAMP production was measured with the Adenylyl Cyclase Activation FlashPlate Assay (NEN Life Science Products, Inc.).

Following transient transfection of the mMCH1R-linker-EGFP construct (MCH-R-1-EGFP) into HEK293 Aequorin cells, the resulting fusion protein exhibited functional activity comparable to that of the wild-type human MCH1R short form (MCH-R wt). By this functional assay, the $EC_{50}$ value for mMCH1R-1-EGFP was nearly identical to that of the wild-type human short form receptor (FIG. 1).

Following transient transfections of the mMCH1R-1-EGFP and mMCH1R/EGFP fusion constructs into CHO cells, the resulting fusion proteins exhibited functional activity comparable to that of the wild-type human MCH1R short form. By this functional assay, the $EC_{50}$ values for mMCH1R-1-EGFP and mMCH1R/EGFP were comparable to that of the wild-type human receptor (Table 1). Transient transfections with the corresponding Emerald constructs yielded similar results (data not shown).

TABLE 1

| Receptor | $EC_{50}$ (nM) |
| --- | --- |
| Wild-type Human MCH1R Short Form | 2.166 |
| Mouse MCH1R/EGFP | 0.819 |
| Mouse MCH1R-1-EGFP | 3.199 |

Following transient transfections of the human short form/mouse species chimeric MCH1R-1-EGFP (HuShort/mMCH1R-1-EGFP) and human long form/mouse species chimeric MCH1R-1-EGFP (HuLong/mMCH1R-1-EGFP) constructs into HEK293 cells, the resulting fusion proteins exhibited functional activity comparable to that of the wild-type human MHC1R short and long forms, respectively. By this functional assay, the $EC_{50}$ value for each fusion proteins was nearly identical to that of the corresponding wild-type human receptor (Table 2).

TABLE 2

| Receptor | $EC_{50}$ (nM) |
| --- | --- |
| Wild-type Human MCH1R Short Form | 22.27 |
| HuShort/mMCH1R-1-EGFP | 19.54 |
| Wild-type Human MCH1R Long Form | 196.7 |
| HuLong/mMCH1R-1-EGFP Form | 217.5 |

Following transient transfections of the human short form/mouse species chimeric MCH1R-1-EGFP (HuShort/mMCH1R-1-EGFP) and human long form/mouse species chimeric MCH1R-1-EGFP (HuLong/mMCH1R-1-EGFP) constructs into CHO cells, the resulting fusion proteins exhibited functional activity comparable to or less than that of the wild-type human MHC1R short and long forms, respectively (Table 3). By this functional assay, the $EC_{50}$ value for the human short form/mouse species chimeric MCH1R-1-EGFP fusion protein was comparable to that of the corresponding wild-type human receptor, whereas, the human long form/mouse species chimeric MCH1R-1-EGFP fusion protein had an $EC_{50}$ value approximately 7.5-fold higher than that of its corresponding wild-type control.

TABLE 3

| Receptor | $EC_{50}$ (nM) |
| --- | --- |
| Wild-type Human MCH1R Short Form | 1.029 |
| Wild-type Human MCH1R Long Form | 1.515 |
| HuShort/mMCH1R-1-EFGP | 1.565 |
| HuLong/mMCH1R-1-EGFP | 11.580 |

Transient expression of all the MCH1R/GFP variant fusion proteins that underwent functional evaluation resulted in fluorescence primarily associated with the plasma membrane in both HEK293 and CHO cells (data not shown). This pattern of fluorescence is consistent with a predominant membrane associated localization.

Example 4

Generation of Stable Cell Lines

Wild-type CHO cells were transfected using SuperFect (Qiag.en) and either mouse MCH-1R-EGFP or human short/mouse species chimeric MCH-1R-EGFP. Forty-eight hours after transfection, transfected cells were subjected to positive selection for approximately ten days in media containing G418. Following selection, MCH-1R-EGFP expressing CHO cells were bulk sorted by Fluorescence Assisted Cell Sorting (FACS) for one or two rounds on the basis of fluorescence intensity to increase the population of cells expressing EGFP. Following bulk sorts, individual clones of varying fluorescence intensities were isolated by FACS and expanded.

Fluorometric Microvolume Assay Technology (FMAT) was initially employed to screen a large number of stable clones by whole cell binding with a fluorescently labeled MCH derivative (SymJz-MCH, PE Biosystems) to identify those clones with good specific binding windows. Several clones exhibiting specific binding windows greater than 3-fold were further evaluated for MCH binding with the SPA-based Binding Assay. Cells from individual clones were dissociated in enzyme free dissociation media and cell membranes were prepared and subsequently tested for their ability to bind $[^{125}I]Phe^{13}Tyr^{19}$-MCH in the presence of human MCH. CHO cell lines expressing either mouse MCH-1R-EGFP or human short/mouse species chimeric MCH-1R-EGFP (FIG. 4) displayed IC50 values with MCH that were indistinguishable from the corresponding IC50 values obtained with a CHO cell line expressing the wild-type human short isoform of MCH-1R.

Figure 2:
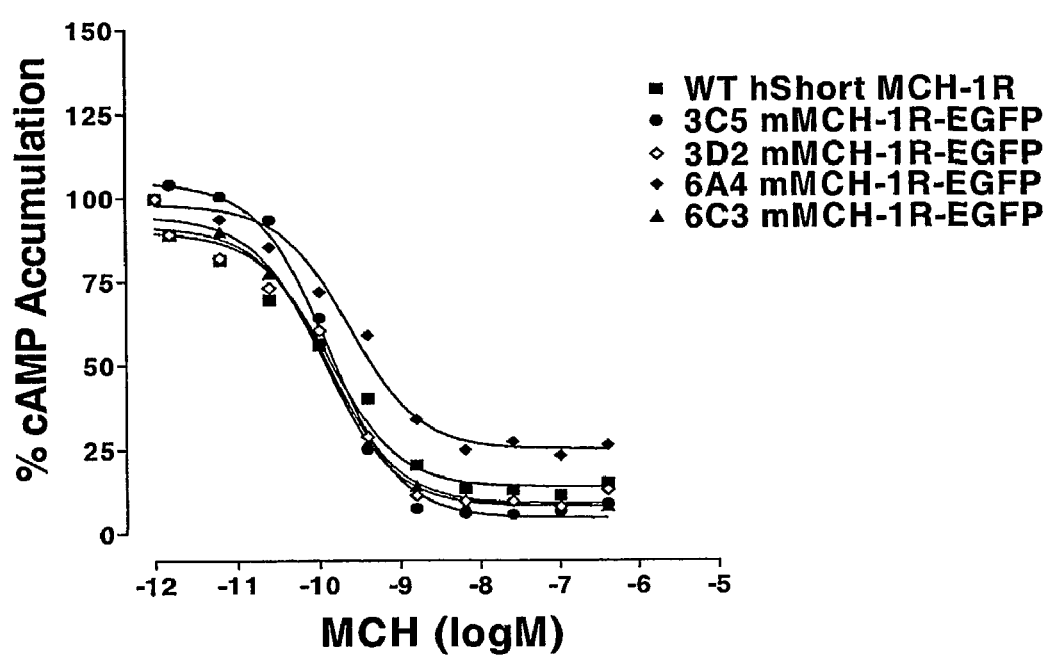
FIG. 2 illustrates a cAMP flashplate assay of CHO cell clones stably expressing mMCH-1R-EGFP. Cells from individual clones were dissociated in enzyme free media and stimulated for 15 minutes at 37° C. with human MCH at the indicated concentrations in the presence of 10 µM forskolin. Cells were then lysed and assayed for bound [$^{125}$I]cAMP. Mouse MCH-1R-EGFP clones exhibited EC50 values (0.1111, 0.1255, 0.1291, or 0.2304 nM) indistinguishable from that of a CHO cell clone expressing the wild-type human short isoform of MCH-1R ( 0.1282 nM).
Figure 3:
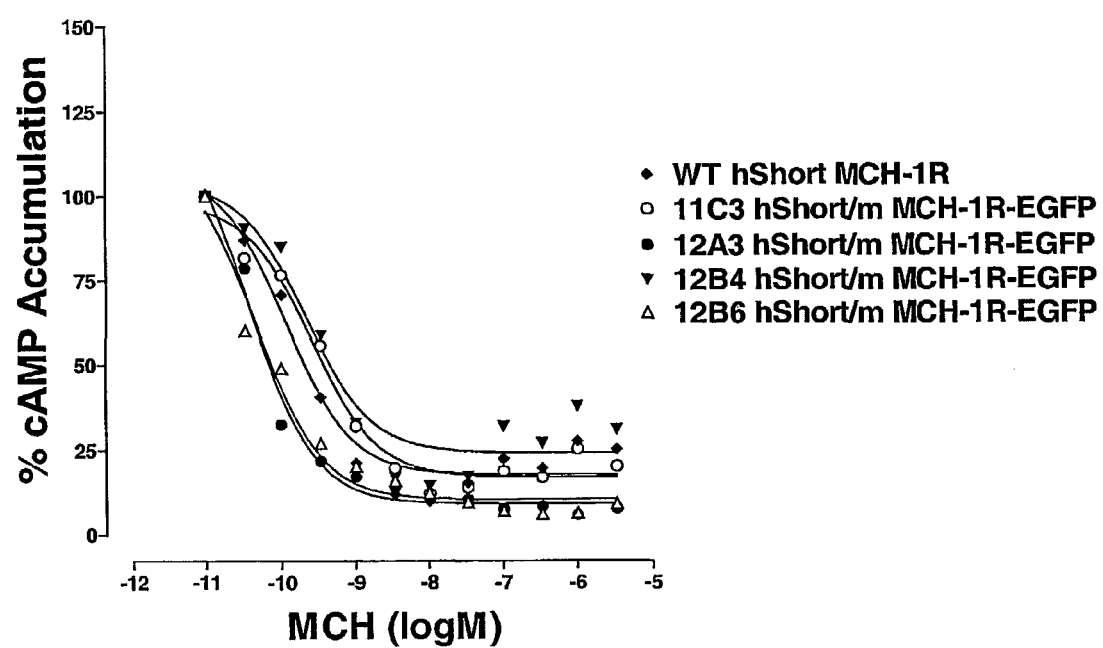
FIG. 3 illustrates a cAMP flashplate assay of CHO cell clones stably expressing human short/mouse species chimeric MCH-1R-EGFP. Cells from individual clones were dissociated in enzyme free media and stimulated for 15 minutes at 37° C. with human MCH at the indicated concentrations in the presence of 10 µM forskolin. Cells were then lysed and assayed for bound [$^{125}$I]cAMP. Human short/mouse species chimeric MCH-1R-EGFP clones exhibited EC50 values (0.0366, 0.0462, 0.2117, or 0.2499 nM) indistinguishable from that of a CHO cell clone expressing the wild-type human short isoform of MCH-1R (0.1137 nM).

The functional activity of these clones was evaluated with the cAMP Flashplate Assay (FIGS. 2 and 3). CHO cell lines expressing either mouse MCH-1R-EGFP (FIG. 2) or human short/mouse species chimeric MCH-1R-EGFP (FIG. 3) displayed EC50 values with human MCH that were indistinguishable from the EC50 value obtained with a CHO cell line expressing the wild-type human short isoform of MCH-1R.

The subcellular localization of the MCH-1R-EGFP fusion proteins were determined by confocal microscopy utilizing EGFP fluorescence as a marker for MCH-1R expression. CHO cell lines stably expressing either mouse MCH-1R-EGFP or human short/mouse species chimeric MCH-1R-EGFP displayed EGFP fluorescence primarily associated with the plasma membrane, demonstrating that these MCH-1R-EGFP fusion proteins are primarily associated with the plasma membrane.

Other embodiments are within the following claims. While several embodiments have been shown and described, various modifications may be made without departing from the spirit and scope of the present invention.

What is claimed is:

1. A protein comprising a melanin concentrating hormone receptor polypeptide region selected from the group consisting of: SEQ ID NO: 4, SEQ ID NO: 5 or SEQ ID NO: 11.

2. The protein of claim 1, wherein said melanin concentrating hormone receptor polypeptide region consists of SEQ ID NO: 5.

3. The protein of claim 2, wherein said protein further comprises a fluorescent polypeptide region joined directly, or though a linker, to the carboxy side of said melanin concentrating hormone receptor polypeptide region.

4. The protein of claim 1, wherein protein consists of the amino acid sequence of SEQ ID NO: 13.

5. The protein of claim 1, wherein said protein consists of the amino acid sequence of SEQ ID NO: 14.

6. A nucleic acid comprising a nucleotide sequence encoding a protein comprising a melanin concentrating hormone receptor polypeptide region selected from the group consisting of: SEQ ID NO: 4 and SEQ ID NO: 5.

7. The nucleic acid of claim 6, wherein said melanin concentrating hormone receptor polypeptide region consists of SEQ ID NO: 5.

8. The nucleic acid of claim 6, wherein said protein further comprises a fluorescent polypeptide region joined directly, or though a linker, to the carboxy side of said melanin concentrating hormone receptor polypeptide region.

9. The nucleic acid of claim 6, wherein protein consists of the amino acid sequence of SEQ ID NO: 13 or SEQ ID NO: 14.

10. The nucleic acid of claim 6, wherein said nucleic acid is an expression vector.

11. The nucleic acid of claim 9, wherein said nucleic acid is an expression vector.

12. A recombinant cell comprising the nucleic acid of claim 6.

13. A recombinant cell comprising the nucleic acid of claim 9.

14. A recombinant cell comprising the expression vector of claim 10.

15. A recombinant cell comprising the expression vector of claim 11.

16. A method for assaying for melanin concentrating hormone receptor active compounds comprising the steps of:
   a) contacting a recombinant cell with a test preparation comprising one or more test compounds, wherein said recombinant cell comprises a nucleotide sequence encoding a protein comprising a melanin concentrating hormone receptor polypeptide region selected from the group consisting of: SEQ ID NO: 4 and SEQ ID NO: 5; and
   b) measuring the effect of said test preparation on one or more melanin concentrating hormone receptor activities.

17. The method of claim 16, wherein said melanin concentrating hormone receptor polypeptide region consists of SEQ ID NO: 5.

18. The method of claim 16, wherein said protein further comprises a fluorescent polypeptide region joined directly, or though a linker, to the carboxy side of said melanin concentrating hormone receptor polypeptide region.

19. The method of claim 16, wherein said protein consists of the amino acid sequence of SEQ ID NO: 13 or SEQ ID NO: 14.

\* \* \* \* \*